US008815556B2

(12) United States Patent
Gourdie et al.

(10) Patent No.: US 8,815,556 B2
(45) Date of Patent: Aug. 26, 2014

(54) COMPOSITIONS AND METHODS FOR TISSUE ENGINEERING, TISSUE REGENERATION AND WOUND HEALING

(71) Applicant: Medical University of South Carolina, Charleson, SC (US)

(72) Inventors: Robert G. Gourdie, Charleston, SC (US); Jay D. Potts, Columbia, SC (US)

( * ) Notice: Subject to any disclaimer, the term of this patent is extended or adjusted under 35 U.S.C. 154(b) by 0 days.

(21) Appl. No.: 13/854,480

(22) Filed: Apr. 1, 2013

(65) Prior Publication Data

US 2013/0236431 A1 Sep. 12, 2013

Related U.S. Application Data

(63) Continuation of application No. 12/896,196, filed on Oct. 1, 2010, now Pat. No. 8,409,603.

(60) Provisional application No. 61/247,806, filed on Oct. 1, 2009, provisional application No. 61/316,550, filed on Mar. 23, 2010.

(51) Int. Cl.
*C12N 11/00* (2006.01)
*C12N 11/16* (2006.01)
*C12N 11/04* (2006.01)
*C12N 5/071* (2010.01)
*C12N 5/00* (2006.01)
*C12N 5/02* (2006.01)

(52) U.S. Cl.
USPC ............ 435/174; 435/182; 435/372; 435/397

(58) Field of Classification Search
USPC .................................. 435/174, 182, 372, 397
See application file for complete search history.

(56) References Cited

FOREIGN PATENT DOCUMENTS

EP          0045665        2/1982

OTHER PUBLICATIONS

Liu, 2006, Tissue Engineering, 12:3405-3416.*
Ghourdie, Ann. NY Acad Sci, 2006, 1080:49-62.*
Savagner, Bioessays, 2001, 23:912-923.*
Kalluri, J Clin Invest. Jun. 1, 2009; 119(6): 1420-1428.*
Liu, 2006, Journal of Surgical Research 136: 336-341.*
Rhett, 2008, Trends in Biotechnology, 26:173-180.*
Almquist et al., "Synthesis and Biological Activity of a Ketomethylene Analog of a Tripeptide Inhibitor of Angiotensin Converting Enzyme", Journal of Medicinal Chemistry, 1980, vol. 23, No. 12, pp. 1392-1398.
Alonso et al., "Stem Cells of the Skin Epithelium", Proceedings of the National Academy of Sciences of the United States of America, Sep. 2003, vol. 100 (Suppl. 1), pp. 11830-11835.
Anthony-Cahill et al., "Site Specific Mutagenesis with Unnatural Amino Acids", Trends in Biochemical Sciences, vol. 14, No. 10, Oct. 1989, pp. 400-403.
Ben-Bassat et al., "Processing of the Initiation Methionine from Proteins: Properties of the *Escherichia Coli* Methionine Aminopeptidase and its Gene Structure" Journal of Bacteriology, vol. 169, No. 2, Feb. 1987, pp. 751-757.
Benner, "Expanding the Genetic Lexicon: Incorporating Non-Standard Amino Acids into Proteins by Ribosome-Based Synthesis", Trends in Biotechnology, vol. 12, No. 5, May 1994, pp. 158-163.
Chan et al., "Live Cell Imaging Distinguishes Bona Fide Human iPS Cells from Partially Reprogrammed Cells", Nature Biotechnology, 2009, vol. 27, No. 11, pp. 1033-1037.
Chen et al., "2009 E-Abstract First Author Index", Investigative Opthalmology and Visual Science, May 2009, vol. 50, No. 5, pp. 2465-2546.
Dai et al., "Cx43 Mediates TGF-Beta Signaling Through Competitive Smads Binding to Microtubules", Molecular Biology of the Cell, Jun. 2007, vol. 18, No. 6, pp. 2264-2273.
Fu et al., "CCN3 (Nov) Interacts with Connexin43 in C6 Glioma Cells: Possible Mechanism of Connexin-Mediated Growth Suppression", The Journal of Biological Chemistry, Aug. 2004, vol. 279, No. 35, pp. 36943-36950.
Ghannam et al., "Immunosuppression by Mesenchymal Stem Cells: Mechanisms and Clinical Applications", Stem Cell Research & Therapy, Mar. 2010, vol. 1, No, 2, 7 pages.
Goodenough et al., "Beyond the Gap: Functions of Unpaired Connexon Channels", Nature Reviews: Molecular Cell Biology Apr. 2003, vol. 4, No. 4, pp. 285-294.
Hann, "On the Double Bond Isostere of the Peptide Bond: Preparation of an Enkephalin Analogue ", Journal of the Chemical Society, Perkin Transactions, Part I, 1982, pp. 307-314.
Holladay et al., "Synthesis of Hydroxyethylene and Ketomethylene Dipeptide Isosteres", Tetrahedron. Letters, 1983, vol. 24, No. 41, pp. 4401-4404.
Hruby. "Conformational Restrictions of Biologically Active Peptides via Amino Acid Side Chain Groups", Life Science, Jul. 1982, vol. 31, No, 3, pp. 189-199.
Hudson et al., "Methionine Enkephalin and Isosteric Analogues Part I, Synthesis on a Phenolic Resin Support", International Journal of Peptide and Protein Research, Sep. 1979, vol. 14, No. 3, pp. 177-185.
Ibba, "Strategies for in vitro and in vivo Translation with Non-Natural Amino Acids", Biotechnology & Genetic Engineering Reviews, vol. 13, Dec. 1995, pp. 197-216.
Ibba et al., "Towards Engineering Proteins by Site-Directed Incorporation in vivo of Non-Natural Amino Acids", Nature Biotechnology, vol. 12, No. 7, 1994, pp. 678-682.
Jaeger et al., "Improved Predictions of Secondary Structures for RNA ", Proceedings of the National Academy of Science of the United States of America, Oct. 1989, vol. 86,No. 20, pp. 7706-7710.
Jaeger et al., "Predicting Optimal and Suboptimal Secondary Structure for RNA", Methods Enzymology, 1989, vol. 183, pp. 281-306.
Jennings-White et al., "Synthesis of Ketomethylene Analogs of Dipeptides", Tetrahedron Letters, 1982, vol. 23, No. 25, pp. 2533-2534.
Jones et al., "In vivo measurement of neutrophil activity in experimental lung inflammation", American Journal of Respiratory and Critical Care Medicine, vol. 149, No. 6, Jun. 1994, pp. 1635-1639.

(Continued)

*Primary Examiner* — Valarie Bertoglio
(74) *Attorney, Agent, or Firm* — Dority & Manning, PA

(57) ABSTRACT

In accordance with certain embodiments of the present disclosure, a kit is described. The kit includes primed living cells joined to and at least partially within a three-dimensional hydrogel structure and an isolated polypeptide having the carboxy-terminal amino acid sequence of an alpha Connexin, or a conservative variant thereof, wherein the polypeptide does not include the full length alpha Connexin protein.

2 Claims, 13 Drawing Sheets

(56) References Cited

OTHER PUBLICATIONS

Khattak et al., "Pluronic F127 as a Cell Encapsulation Material: Utilization of Membrane-Stabilizing Agents", Tissue Engineering, Jul. 2005, vol. 11, No. 5-6, pp. 974-983.

Martin et al., "Actin Cables and Epidermal Movement in Embryonic Wound Healing", Nature, Nov. 1992, vol. 360, No. 6400, pp. 179-183.

Martin et al., "Pulsed Contractions of an Action-Myosin Network Drive Apical Constriction", Nature, Jan. 2009, vol. 457, No. 7228, pp. 495-499.

Millikan, "Incisional Hernia Repair", Surgical Clinics of North America, vol. 83, No. 5, Oct. 2003, pp. 1223-1234.

Morley, "Modulation of the action of regulatory peptides by structural modification", Trends in Pharmacology Sciences, 1980, vol. 1, No. 2, pp. 463-468.

Mudge et al., "Incisional Hernia: A 10-year Prospective Study of Incidence and Attitudes", The British Journal of Surgery, Jan. 1985, vol. 72, No. 1, pp. 70-71.

Needleman et al., "A General Method Applicable to the Search for Similarities in the Amino Acid Sequence of Two Proteins", Journal of Molecular Biology, Mar. 1970, vol. 48, No. 3, pp. 443-453.

O'Quinn et al., "Abstract 3866: A Peptide Containing the Carboxy-Terminal Domain of Connexin43 Reduces Arrhythmias and Improves Cardiac Function after Myocardial Injury", Circulation, 2008, vol. 118, pp. S_495.

O'Regan et al., "Cloning and Nucleotide Sequence of the Phosphoenolpyruvate Carboxylase-Coding Gene of Corynebacterium Glutamicum ATCC13032", Gene, vol. 77, No. 2, Apr. 1989, pp. 237-251.

Pearson et al., "Improved Tools for Biological Sequence Comparison", Proceedings of the National Academy of Science of the United States of America, Apr. 1988, vol. 85, No. 8, pp. 2444-2448.

Rizo et al., "Constrained Peptides: Models of Bioactive Peptides and Protein Substructures", Annual Review of Biochemistry, Jul. 1992, vol. 61, pp. 387-418.

Sahin-Toth et al., "Cysteine Scanning Mutagenesis of the N-Terminal 32 Amino Acid Residues in the Lactose Permease of *Escherichia Coli*", Protein Science, Feb. 1994, vol. 3, No. 2, pp. 240-247.

Smith et al., "Comparison of Biosequences", Advances in Applied Mathematics, Dec. 1982, vol. 2, No. 4, pp. 482-489.

Songyang et al., "Recognition of Unique Carboxyl-Terminal Motifs by Distinct PDZ Domains", Science, Jan. 1997, vol. 275, No. 5296, pp. 73-77.

Spatola, "Peptide Backbone Modifications: A Structure-Activity Analysis of Peptides Containing Amide Bond Surrogates, Conformational Constraints and Relations", Chemistry and Biochemistry of Amino Acids, Peptides, and Proteins, 1983, vol. 7, (B. Weinstein, ed.), Marcel Dekker, New York, p. 267-357.

Spatola et al., "Structure-Activity Relationships of Enkephalins Containing Serially Replaced Thiomethylene Amide Bond Surrogates", Life Sciences, Apr. 1986, vol. 38, No. 14. pp. 1243-1249.

Sribnick et al, "Estrogen Treatment of Spinal Cord Injury Attenuates Calpain Activation and Apoptosis", Journal of Neuroscience Research, Oct. 2006, vol. 84, No. 5, pp. 1064-1075.

Takahashi et al., "Induction of Pluripotent Stem Cells from Mouse Embryonic and Adult Fibroblast Cultures by Defined Factors", Cell, Aug. 2006, vol. 126, No. 4, pp. 663-676.

Thorson et al., "A Biosynthetic Approach for the Incorporation of Unnatural Amino Acids into Proteins", Methods in Molecular Biology, 1991, vol. 77, pp. 43-73.

Toyofuku et al., "Direct Association of the Gap Junction Protein Connexin-43 with ZO-1 in Cardiac Myocytes", The Journal of Biological Chemistry, May 1998, vol. 273, No. 21, pp. 12725-12731.

Wada et al., "Epicardial/Mesothelial Cell Line Retains Vasculogenic Potential of Embryonic Epicardium", Circulation Research, Mar. 2003, vol. 92, No. 5, pp. 525-531.

Wilgus et al., "Reduction of scar formation in full-thickness wounds with topical celecoxib treatment", Wound Repair Regeneration, Feb. 2003, vol. 11, No. 1, pp. 25-34.

Zoller, "New Recombinant DNA Methodology for Protein Engineering", Current Opinion in Biotechnology, vol. 3, No. 4, Aug. 1992, pp. 348-354.

Zuker, "On Finding all Suboptimal Foldings of an RNA Molecule", Science, Apr. 1989, vol. 244, No. 4900, pp. 48-52.

* cited by examiner

COMPOSITIONS AND METHODS FOR TISSUE ENGINEERING, TISSUE REGENERATION AND WOUND HEALING

FEDERALLY SPONSORED RESEARCH

This invention was made with government support under 2P20RR016434-06 awarded by the National Institutes of Health. The government retains certain rights in the invention.

CROSS REFERENCE TO RELATED APPLICATIONS

The present application is a continuation of U.S. application Ser. No. 12/896,196 having a filing date of Oct. 1, 2010 (allowed and issued as U.S. Pat. No. 8,409,603), which is based on and claims priority to U.S. Provisional Application Ser. No. 61/247,806, filed Oct. 1, 2009 and U.S. Provisional Application Ser. No. 61/316,550, filed Mar. 23, 2010, which are incorporated by reference herein in their entirety.

BACKGROUND

Body organs display complex shapes, surfaces and internal structures, including blood vessels. Coupled to morphological complexity, the component tissues of organs possess dynamic contractile and mechanically responsive elements such as sphincter muscles. The ability to accurately recapitulate naturally occurring complexities of shape, internal structure and functionality is a key goal of tissue engineering. Current approaches to this problem include the use of scaffolds to generate in vivo like environments for cell growth or "organ printing" where point-by-point extrusion from a modified ink-jet printer has enabled cells to be precisely arranged into three-dimensional tissue-like structures.

Technologies based on culture scaffolds or organ printing rely on application of straightforward engineering principles. To date, the field has been less successful in harnessing self-organizing processes occurring during embryonic development to elaborate useful biological structure in vitro.

Similarly, a tissue-engineered approach for wound healing attempts to promote regenerative and scar-free healing. In this regard, stem cells are increasingly being utilized as part of regenerative therapies. To date, conventional regenerative therapies based on stem cells involve the introduction of dispersed cells into a diseased organ with little regard for the status of these randomly introduced cells. Current therapies often show marginal, variable, or even controversial propensity to promote regenerative and scar free healing. As such, improvements to available compositions and methods would be beneficial.

The epithelial-mesenchymal transition (EMT) precedes virtually every cellular differentiation in the embryo. For example, during human development one of the first rounds of EMT occurs as part of gastrulation, in which the 3 embryonic germ layers differentiate. Subsequent rounds of EMT within germ layers occur as a prelude to morphogenetic processes as diverse as neurogenesis, myogenesis, and vasculogenesis.

The precise role of EMT is unclear. EMT resembles a priming step that precedes morphogenetic events. Progenitor (i.e., stem) cells form stable cell-cell junctional contacts, synchronizing cytoskeletal organization, polarity, and to some extent proliferative activity. The cells then detach, transforming into invasive mesenchymal cells in a coordinated progression toward terminal differentiation.

The present disclosure describes a unique and non-obvious series of steps to stimulate an EMT-like state in cells in a culture dish (referred to as EMT-priming or activation) to provide: a) microtissue compositions (e.g., toroids of EMT-primed/activated cells) with medical uses in tissue engineering and b) regenerative healing methods and compositions as described in the subsequent text of this disclosure.

SUMMARY

In accordance with certain embodiments of the present disclosure, a kit is described. The kit includes primed living cells joined to and at least partially within a three-dimensional hydrogel structure and an isolated polypeptide having the carboxy-terminal amino acid sequence of an alpha Connexin, or a conservative variant thereof, wherein the polypeptide does not include the full length alpha Connexin protein.

In another embodiment of the present disclosure, a method for forming a hydrogel structure in which living cells are joined thereto is disclosed. The method includes placing living cells on a three-dimensional hydrogel structure. The method further includes permitting epithelialization of the cells in which the cells attach to the surface of the hydrogel structure, undergo epithelial mesenchymal transition, and penetrate the surface of the hydrogel structure.

In still another embodiment of the present disclosure, a method of promoting healing following tissue injury in a subject is disclosed. The method includes administering to the subject's injury primed living cells which are joined to and at least partially within a three-dimensional hydrogel structure and an isolated polypeptide comprising the carboxy-terminal amino acid sequence of an alpha Connexin, or a conservative variant thereof, wherein the polypeptide does not comprise the full length alpha Connexin protein.

Other features and aspects of the present disclosure are discussed in greater detail below.

BRIEF DESCRIPTION OF THE DRAWINGS

A full and enabling disclosure of the present invention is set forth in the specification with reference to the following figures.

DETAILED DESCRIPTION

Figure 1:
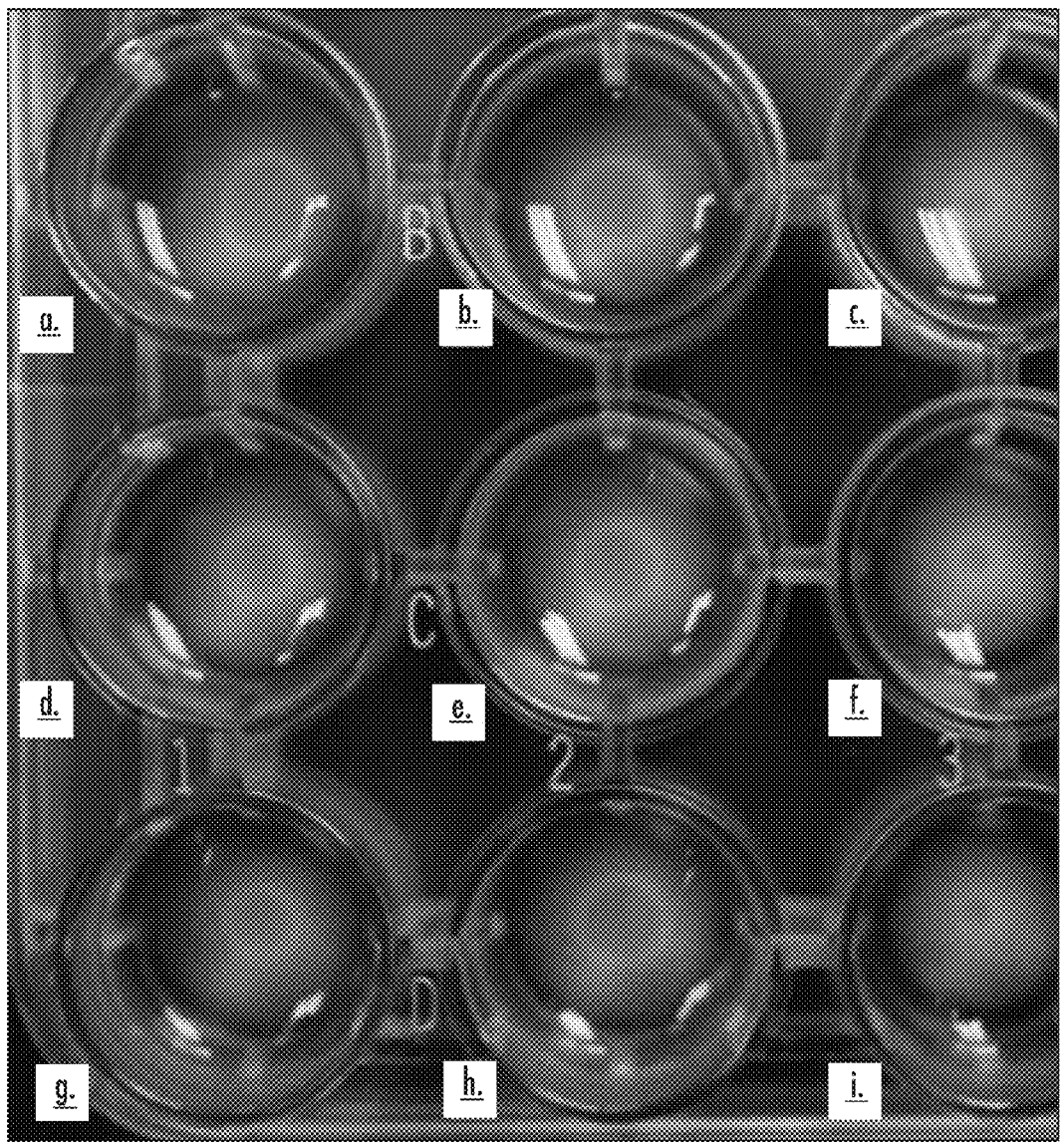
FIG. 1 illustrates examples of toroids generated from EMT-primed lens epithelial cells; a-c) a control series of 3 toroids generated in regular media, d-f) a control series of 3 toroids generated in media containing a control peptide and g-h) a series of 3 toroids generated in media containing a an ACT1 peptide in combination with Tgfb1.
Figure 2:
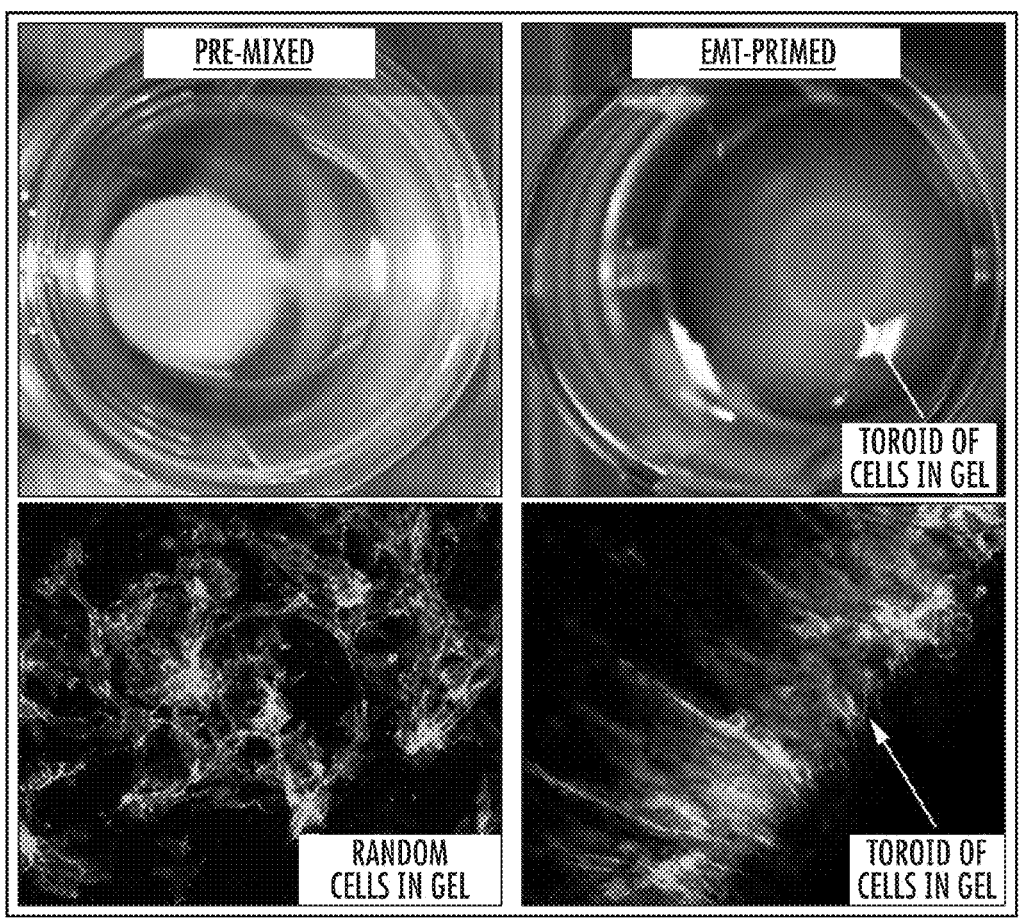
FIG. 2 illustrates examples of gel in which lens epithelial cells (i.e., non-EMT primed) have been premixed into collagen (right hand panels). No toroid forms in this case (upper right hand panel) and the cells within the gel are disorganized (lower right hand panel). A toroid is generated from EMT-primed lens epithelial cells (upper left hand panel); immuno-confocal optical sectioning reveals the cellular composition of the toroidal ring within the gel (lower left hand panel).
Figure 3:
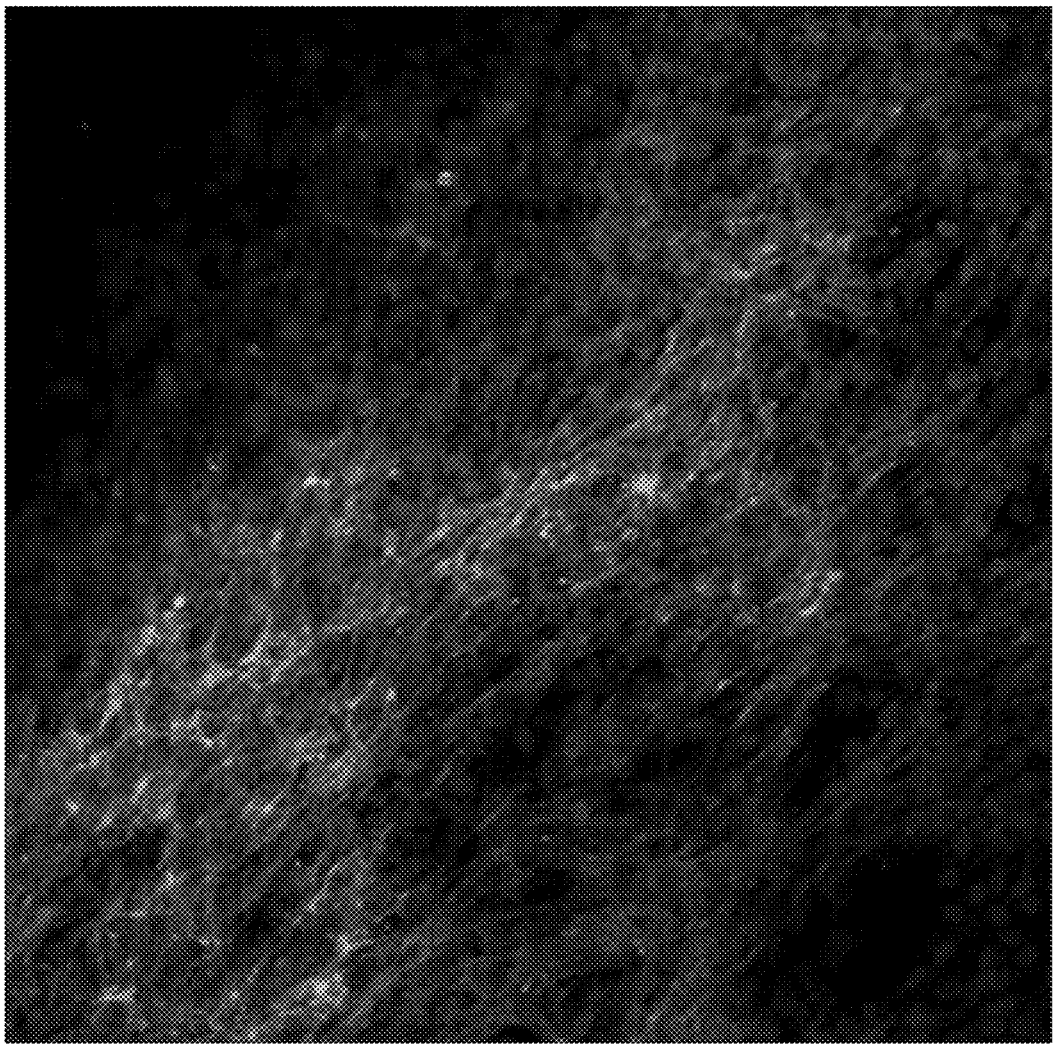
FIG. 3 illustrates a high power view of phalloidin-stained aligned cells in a toroid.

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure describes a simple method for prompting self-organization of cells in gels into repeatable and geometrically distinct microtissue units, including rings and hollow spheroids. For instance, the present disclosure describes methods for generating tissue-engineered rings (also referred to herein as "toroids") of cells in vitro. The methods described herein provide a novel approach to directing self-organizing morphogenetic principles that are intrinsic to three-dimensional networks of cells. These have the potential to be iteratively combined to tissue engineer more complex structures. As a consequence, the microstructure and function of toroids and other structures generated as described in the present disclosure closely resemble naturally occurring complexities of tissues in living organisms, including humans. The methods described herein can also be adjusted to generate other useful objects, including spheroids. Spheroids are generated by using a square gel, rather than one of circular geometry. In other embodiments the starting gel geometry can take a variety of forms and sizes including circular, square, rectangular trapezoid, or any regular of irregular two-dimensional shape. The starting gel can also be in the form of a tube or any other so constrained three-dimensional structure.

In another embodiment, the initial gel used to construct the tissue engineered composition can be a tubular tissue scaffold wherein the wall is comprised of polymer fibrils that are aligned in a helical pattern around the longitudinal axis of the tube where the pitch of the helical pattern changes with the radial position in the tube wall.

In another embodiment, a pattern of stress or strain can be imparted statically, dynamically or in combination on a gel containing cells undergoing EMT-priming to achieve a desired cellular geometry.

In yet another embodiment self-organized toroids generated in accordance with the present disclosure can be used in a tissue-engineered assist composition for wound healing, tissue engineering or regenerative healing or as a scaffold for elaboration of a tissue, such as an artificial venous sphincter muscle. The present disclosure also describes how toroids and other morphogenetically engineered structures generated by the methods described herein can be iteratively stacked, fused or otherwise combined to generate engineered tissues of complex geometry including synthetic blood vessels.

For example, tissue-engineered structures generated by the methods described herein such as toroids or other geometric structures can be combined with each other to form complex three-dimensional arrays, and if required, organ or organ like structures or other biological structures such as a bone and the like. In general, these three-dimensional arrays include two or more layers separately applied to a substrate, with subsequent layers applied to the top surface of lower layers. These tissue engineered organs and biological structures would then be used as a therapy in the regenerative repair of, for example, damaged, diseased or congenitally malformed organs and tissues.

In certain embodiments, the layers can combine or fuse following placement on the substrate or, alternately, remain substantially separate and divided following application. Three-dimensional structures can be formed in a variety of ways in accordance with the present disclosure. For example, three-dimensional arrays can be formed by placing multiple layers onto the substrate using an organ printing device or using a novel device that iteratively combines toroids to build up complex three-dimensional structures by layering one tissue-engineered structure on another in a manner contemplated as being similar to a ham slicer working in reverse. The tissue engineered structures in the layers can be retained in the gel upon iteration into a three dimensional array and or largely separated from the gel, such as would occur if the composition had been generated in thermo-gelling hydrogel.

It is sometimes desired when three-dimensional structures are generated that that any subsequent cell growth is substantially limited to predefined sectors of the structure. Thus, to inhibit or promote growth, promote differentiation, or promote or inhibit apoptosis inside or outside of a predefined region, compounds, devices or the like can be applied to specific regions of substrate to inhibit cell growth, differentiation, or cell death, thus forming a boundary within the structure. Some examples of suitable compounds for this purpose include, but are not limited to, growth factors, cytokines, drugs, agarose, poly(isopropylN-polyacrylamide) gels, and the like. Such factors can be present in some layers and not in others to generate the desired three-dimensional structure.

Figure 5:
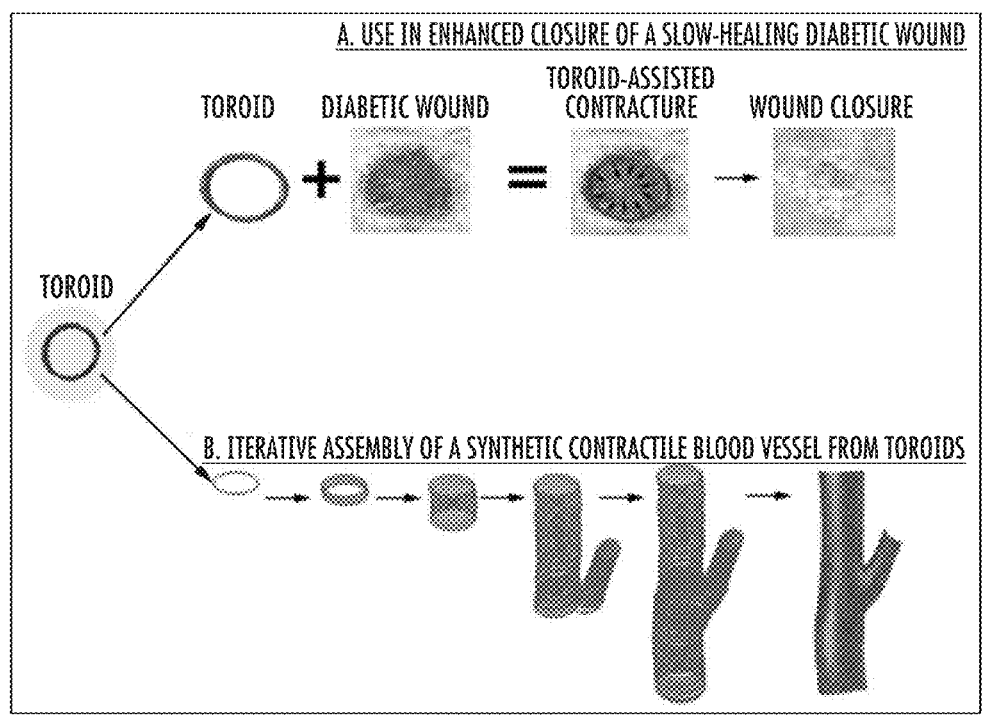
FIG. 5 illustrates hypothetical examples of how toroids can be used to a) enhance wound closure of a slow-healing diabetic wound, b) be assembled iteratively into the branched tubular scaffold of an artificial blood vessel.

In one example of such embodiments, the process of generating a boundary can be employed to form a multi-layered, three-dimensional tube such as a blood vessel (e.g, FIG. 5*b*).

In such embodiments would be desired to generate a growth restricted toroidal layer of endothelial cells within a larger diameter toroid of smooth muscle and then stack such composites to generate a tube. Growth restriction within the endothelial layer prior and during fusion of the layers of the structure would act to prevent the tube that eventually formed from becoming occluded.

In addition to layer-by-layer assembly, three-dimensional arrays can also be formed by placing a single layer of the tissue-engineered compositions onto a substrate. In such embodiments, this layer would be allowed to grow in culture and develop into a single or multi-layered structure. In one simple example, a toroid of endothelial cells can be placed on a substrate within a larger diameter toroid of smooth muscle cells. These composite rings can then be stacked, fused or otherwise combined to generate a blood vessel like tube. In another example, the approach would be used to generate extended two-dimensional layers of fused unitary compositions such as the case if artificial skin was being prepared. In yet a further example, extended two dimensional sheets would be combined with unitary tissue-engineered composition or other similarly manufactured sheet to build up large scale three dimensional structure such as would be required to iterate a large organ such as a liver or distinct biologic structures such as an ear cartilage or a bone. These tissue-engineered structures would then be used as a therapy in the regenerative repair of, for example damaged, diseased or congenitally malformed organs or tissues.

Very generally, one aspect of the present disclosure (i.e., in the generation of an individual tissue engineered composition) is a multi-step process in vitro.

The process includes initiation, which requires placement of dispersed suspensions of living cells on a flexible three-dimensional culture hydrogel that are constrained by adherence to a rigid surface (e.g., the plastic bottom and sides of a circular tissue culture well, or the like). The hydrogel can be composed of collagen in one example (e.g., FIG. 1). The hydrogel can also be composed of keratins, fibrins, chitosans, glycosaminoglycans, elastins, matrigel, carrageenan, chondroitin sulfate, gelatin, pectin, alginate or gels based on combinations of these naturally occurring components), other naturally occurring or synthetic components comprising the gel can include fibronectins, laminins, proteoglycans, hyaluronan, glc-nac, matricellular proteins (e.g., periostins and related polypeptides, CNN1, thrombospondins), collagen or elastin mimetics or combinations thereof, or synthetic hydrogel components (e.g. polyurethane hydrogel, PEG hydrogel, polyacrylate hydrogel, polyvinyl alcohol, sodium polyacrylate, acrylate polymers and copolymers, carboxymethyl or carboxyethyl cellulose or combinations thereof), hybrid hydrogels synthetic or naturally occurring components (e.g., gels composed of collagen and polyethylene glycol (PEG)) and naturally occurring, synthetic or hybrid hyrogels functionalized with drugs, sugars, peptides, particles or other attached or integrated factors and the like.

Other examples of hydrogel materials that can be used alone or in combination with other gel composite materials include polylactic glycolic acid-ethylene glycol-lactic glycolic acid, poly hydroxy butyrate, polypropylene fumarate-co-ethylene glycol, polylactic acid-ethylene glycol-lactic acid, polyethylene glycol-lactic acid-ethyleneglycol, polymethylmethacrylate-co-hyroxyethylmethacrylate, polyethylene glycol-bis-lactic acid-acrylate, polyethylene glycol-butylene oxide-terephtalate, polylactic glycolic acid-c-serine, polyhydroxypropylacrylamide-g-peptide, polyethylene glycol-g-acrylamide-co-vemine, polyethylene glycol/-cyclodextrins, polyvinylacetate/vinylalcohol, polyhydroxyethyl- methacrylate/Matrigel, polyN-vinyl pyrrolidone, polyacrylonitrile-co-allil sulfonate, polyethylene glycol dimethacrylate-sulfate, polyethyleneglycol-co-peptides), polybiscarboxy-phenoxy-phospazene, alginate-gpolyethylene oxide-propylene oxide-ethylene oxide, polyacrylamide, polyN-isopropyl acrylamide-co-acetic acid, polyN-isopropyl acrylamide-co-ethylmethacrylate, chitosan-g-polyethylene oxide-propylene oxide-ethylene oxide, hyaluronic acid-g-N-isopropyl polyacrylamide, alginate-acrylate and collagen-acrylate.

In another example, a hydrogel that can be activated to become fluid by lowering its temperature, to about 25° C. or below (i.e., room temperature). For example, such gels would be used to generate the tissue-engineered composition and then the gel depolymerized by temperature lowering so that the cellular elements of the composition that had been prompted by the methods described herein, to self-organize into the desired geometry, can be isolated from the hydrogel and then fused or otherwise combined to form new compositions as described herein to generate complex three- and two dimensional structures. One example of such multi-dimensional compositions would be tissue engineered organ or organ-like structures used in the regenerative repair of, for example damaged, diseased or congenitally malformed organs.

An example of a thermo-gel is a polymer of a meth-acrylamide derivative and a hydrophilic monomer. A further example of a thermogel hydrogel polymer is a biodegradable polymer containing a polyethylene glycol (PEG) block linked to biodegradable polyester. Other examples are gels based on pluronic acid (PLA) that become liquid at 4 C but form hydrogels at 37 C. These thermogels can also be mixed with other naturally occurring on synthetic hydrogel materials or contain other compounds that improve their performance in generating and maintaining the tissue engineered composition. For example, addition of steroidal hydrocortisone to PLA thermogel improves the viability of cells contained within the gel (Khattak et al. Tissue Eng. 2005 May-June; 11(5-6):974-83, incorporated by reference herein).

The next step of the multi-step sequence required to generate the composition is what is termed epithelialization. Epithelialization refers to a period of culture in which cells to attach to the surface (i.e., the substrate) of the cultured hydrogel and initiate cell-matrix and cell-cell interactions. The epithelial mesenchymal transition (EMT) is one of the most fundamental morphogenetic mechanisms in extant multicellular organisms. During EMT, epithelial cells adherent to a substrate surface transform to assume a migratory and invasive mesenchymal phenotype. In developing vertebrates, cells undergoing EMT include those contributing to gastrulation, neurogenesis, skeletal myogenesis, cardiomyogenesis, and vasculogenesis. EMT is a necessary prelude to basic differentiation processes occurring in the human embryo and also has been shown to have assignments in cancer and in the genesis of stem cells. Thus in certain aspects, the steps of the present disclosure embody reverse engineering of a developmental process to provide a novel composition in a culture dish, a composition, device and method with therapeutic assignments.

A further period of culture takes place in which cells on the culture gel surface undergo an epithelial-mesenchymal-like transformation, invading the gel interior and remodeling cell-cell interactions as this invasive migration proceeds. Three-dimensional cellularization takes place as still a further period of culture occurs in which the cells proliferate, migrate, and differentiate stable new patterns of three-dimensional cell-cell and cell matrix interaction within the cultured gel. Activation of cells to form the unitary microtissue composition is further contributed to by a precisely timed release of the cellularized three-dimensional gel from attachment to its constraint. Lastly, morphogenesis occurs as a further period of culture wherein the cells in the gel undergo a process of re-organization into a ring of aligned and electromechanically coupled contractile cells or other self-organized structure such as a spheroid dependent on the novel inventive steps disclosed herein for directing this morphogenesis-like process in vitro.

Certain aspects of the individual steps and sequence of steps described herein are both necessary and non-obvious aspects of the present disclosure. For instance, if cells are mixed directly into the gel thereby omitting certain other steps, morphogenesis of the cells into a provided complex tissue structure does not proceed and the usefulness of such compositions in methods of regenerative healing as described later in this disclosure are reduced. In one example when stem cells are "pre-mixed" into a collagen gel, as opposed to being activated in vitro as described herein, this "mixed" stem cell composition is not observed to provide benefits to wound healing, scar reduction and tissue regeneration provided by the tissue-engineered composition of EMT-primed stem cells in the disclosure provided herein. Furthermore, EMT-primed BMSCs and other stem cell types can improve immune tolerance of other engrafted tissues, organs, or bioengineered structures. For instance, the literature describes BMSCs having this effect (Ghannam S, Bouffi C, Djouad F, Jorgensen C, Noël D. Immunosuppression by mesenchymal stem cells: mechanisms and clinical applications. Stem Cell Res Ther. 2010 Mar. 15; 1(1):2., incorporated by reference herein).

Figure 4:
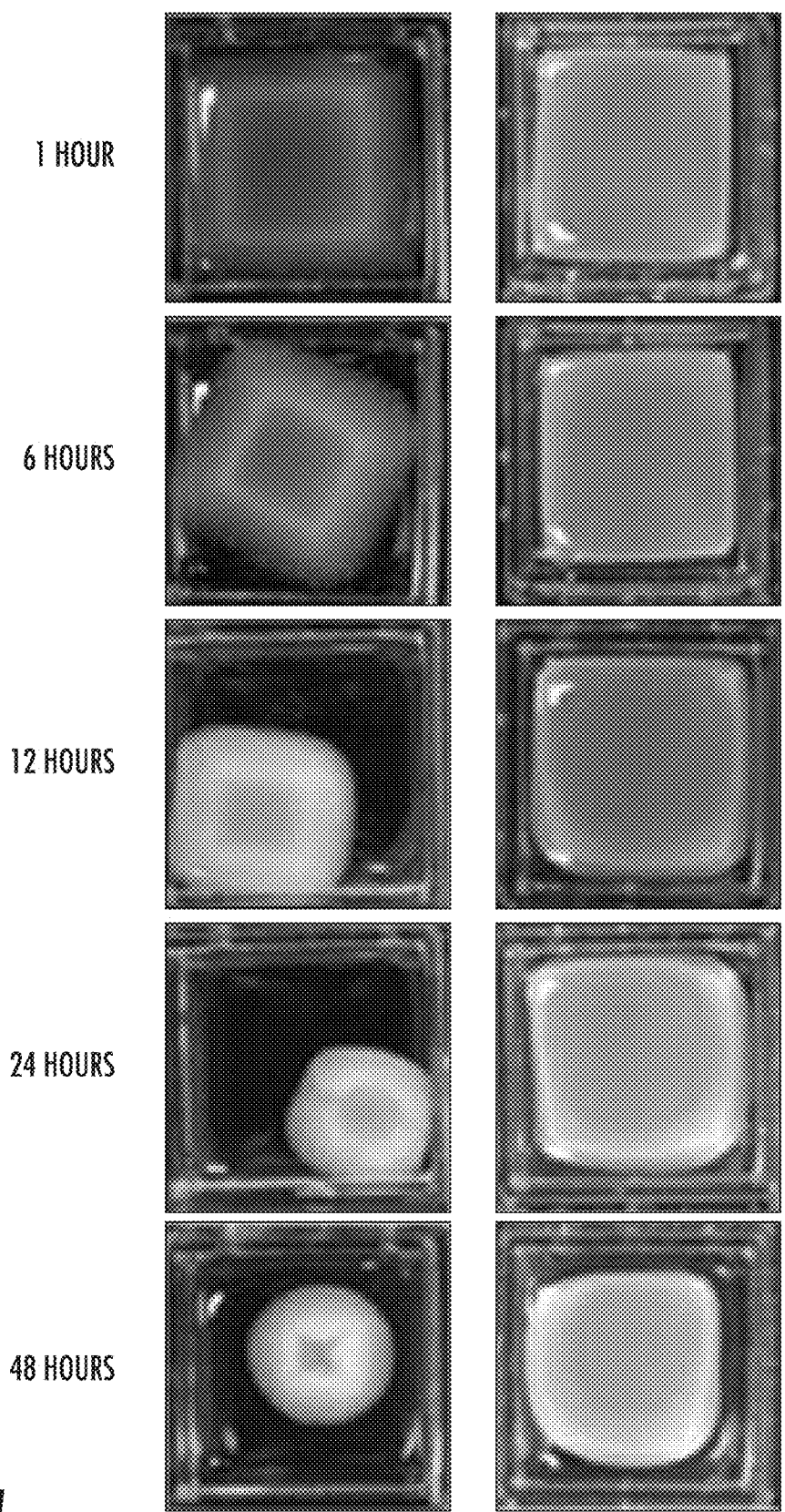
FIG. 4 illustrates a) examples of "apertured" spheroids formed by adjustment of the initial geometry of constraint of the gel over a 48 hour time course, b) if the cells are pre-mixed into the gel, morphogenesis into a spheroid does not proceed.

It should be understood, however, that various modifications to the process described herein are contemplated in accordance with the present disclosure. For example, the present disclosure contemplates that tissue-engineered toroids of smaller and larger diameter (e.g., ~1 mm to 3-5 cm and in a larger example structures of about up to 10 cm) will be generated by modifying certain parameters including the diameter of the culture well, cell number at initiation, and the physical and chemical properties of the gel. Similarly, different constructs including oblong rings, irregular rings and even hollow shapes such as spheres, ovoids and other irregular geometries will be generated by modifications that include adjustment of the initial pattern of rigid constraint, adjustment of parameters described previously, and/or manipulation of the timing of gel release and adjustment of the physical and chemical regularity of the gel. As an example, FIG. 4a shows hollow spheroids, each with a small aperture that were generated in a square-sided well.

Similarly, while a gel-based method is simple and convenient, the present disclosure contemplates that synchronization and activation of epithelial-mesenchymal-like transformation is achievable in receptive cells by other means including via genetic, pharmaceutical, and/or chemical manipulations. It is understood that the present disclosure primarily demonstrates the need for recapitulation of synchronization and activation in EMT-like morphogenesis in vitro, prior to uses that include generation of complex three-dimensional structures from microtissue units or transplantation into a wound.

Various cell types are contemplated by the present disclosure including epithelial cells, mesenchymal cells, endothelial cells, bone marrow cells, spleen cells, lymphatic cells, stem cells, progenitor cells (natural or induced), all embryonic, postnatal and adult derivatives of endoderm, mesoderm or ectoderm cells, vascular cells, muscular cells, mesenchymal cells, hematopoietic cells, fibroblasts, myofibroblasts, osteogenic cells, fibrogenic cells, neurogenic cells, myogenic cells, smooth muscle cells, cardiomyocytes, and combinations thereof.

Other examples include Keratinizing epithelial cells: e.g., Epidermal keratinocyte, Epidermal basal, Nail bed basal, and Hair matrix cells; Wet stratified barrier epithelial cells: e.g., epithelial cells of stratified squamous epithelium of cornea, tongue, oral cavity, esophagus, anal canal, distal urethra and vagina and basals cells of the same tissues; Gland cells; e.g., Exocrine secretory epithelial cells; e.g., Hormone secreting cells, including Anterior pituitary, Intermediate pituitary cell, secreting melanocyte-stimulating hormone, Magnocellular neurosecretory, Gut and respiratory tract, Thyroid gland cells, Parathyroid gland cells, Adrenal gland, Leydig, Juxtaglomerular, Macula densa, Peripolar cell and Mesangial cells; Metabolism and storage cells: e.g., Hepatocyte, White fat and Brown fat cells and lipocytes; Barrier function cells of Lung, Gut, Exocrine Glands and Urogenital Tract, Epithelial cells lining closed internal body cavities: e.g., Blood vessel and lymphatic vascular endothelial fenestrated cell, Blood vessel and lymphatic vascular endothelial continuous cell, Blood vessel and lymphatic vascular endothelial splenic cell, Choroid plexus cell, Pigmented ciliary epithelium cell of eye, Nonpigmented ciliary epithelium cell of eye, Corneal endothelial cell; Ciliated cells with propulsive function: e.g., Respiratory tract ciliated cell; Extracellular matrix secretion cells: e.g., Ameloblast epithelial, Planum semilunatum epithelial cell, Loose connective tissue, Corneal, Tendon, Bone marrow and Other nonepithelial fibroblasts, Pericytes, chondrocytes, Osteoblast/osteocyte, Osteoprogenitor cells, Hyalocyte of vitreous body, and Stellate cells; Contractile cells: Skeletal muscle and Satellite cells (stem cell) and Heart muscle stem cells, Smooth muscle cells, Myoepithelial cells, Blood and immune system cells; e.g., leukocytes, monocytes, cell of the nervous system e.g., Astrocytes, Neurons, and Oligodendrocytes, Anterior lens epithelial cell, Pigment cells, Germ cells, Nurse cells and Interstitial cells. Progenitor and embryonic cells as well as committed progenitors of forementioned cell types provided in this paragraph.

These and other cell types will be able to sufficiently model the process described herein such that the aforementioned structures will also form from these cell types. It is furthermore anticipated that two or more different cell types can be mixed in the same gel to differentiate the aforementioned structures comprised of one or more cell types.

It is also anticipated that any cell type receptive to synchronization and activation by the provided method should be a sufficient substrate for inducing the regenerative healing benefit described herein. Stem cells are probably especially receptive, as such bone-marrow derived stem cells (BMSCs) can be substituted by other stem cell types including totipotent, omnipotent, pluripotent, multipotent, oligopotent and unipotent stem cell types, including embryonic, fetal, and adults stem cells, amniotic stem cells and other stem cells derived from the various stem cell niches and fluids found within or emanating from the human body, mesenchymal stem cells, tissue and lineage specific stem cells and induced progenitor stem cells. Other differentiated cell types should also provide benefit following induction in vitro by the present method, particularly if it is combined with a regimen that reverts these cells to induced pluripotent stem cells (iPS) or iPS-like state.

In addition, targeted treatments with drugs, cytokines, chemicals, and other bioactive substances will provide a further way of modulating and directing the differentiation of the aforementioned structures (e.g. FIGS. 1g-h). For instance, a treatment of skin wounds with a toroid of BMSCs and ACT1 significantly enhances regenerative healing and inhibits scarring over that occurring for treatments with a BMSC toroid alone or the peptide alone. In another example, treatment of skin wounds with a toroid of BMSCs and TGF-beta3 significantly enhances regenerative healing and inhibits scarring over that occurring for treatments with a BMSC toroid alone or the peptide alone. TGF-B3 and/or ACT1 can be used coincident with or after the injury or can be introduced to a site on the subject prior to a surgery or any anticipated tissue-disrupting procedure (e.g., non-surgical dermabrasion) in order to precondition the site for the purpose of scar reduction, improved tissue structure and function and regenerative repair. The pre-conditioning can be at or repeated at 1, 2, 3, 4, 5, 6 hours or any other interval up to 24 hours. The pre-conditioning can be at or repeated at 1, 2, 3, 4, 5, 6 or any other interval up to 48, 72, and 96 hours and up to a week. Following preconditioning and surgery further post-treatment with the invention or constituents (TGF-B3 or ACT1) can be undertaken. BMSCs not induced to organize into the provided compositions did not show propensity to promote regenerative and scar-free healing. The present composition and method, involving the artificial generation of a primitive embryonal-like tissue in vitro and the transplantation of this tissue into a wound, embodies a novel therapeutic approach that conveniently recapitulates embryonal scarless healing in the postnate or adult.

The present disclosure contemplates combination of the provided composition with treatments or pre-conditioning treatments other than ACT1 and TGF-beta3 known to improve healing and/or reduce scarring including osteopontin, platelet-derived growth factor (PDGF), transforming growth factor and beta, TGFb or Cx43 antisense or peptides can be of significant benefit. Other molecules that are contemplated for use with the present disclosure include bone morphogenetic proteins (BMP), epidermal growth factors (EGF), erythropoietins (EPO), fibroblast growth factors (FGF), platelet derived growth factors (PDGFs), ligands for the seven transmembrane helix family, granulocyte-colony stimulating factor (GCSF), granulocyte-macrophage colony-stimulating factor (GMCSF), growth differentiation factor-9 (GDF9), hepatocyte growth factor (HGF), hepatoma derived growth factor (HDGF), human growth hormones (HGH), interleukins (IL), insulin growth factors (IGF), insulin growth factor binding proteins (IGFBP), myostatins (GDF-8), nerve growth factors (NGF) and other neurotrophins, thrombopoietins (TPO), vascular endothelial growth factors (VEGF), transglutmaninases, caveolins, matricellular proteins (e.g., periostin, CCNs, thrombospondins), osteopontin, canonical (e.g., Wntl, Wnt3a) and non-canonical WNTs (e.g., Wnt5a, Wnt11), planar cell polarity pathway signaling components, interleukins, tumor necrosis factors (TNFs), Notch-Delta, hyaluronin and related molecules, Hyaluronic synthetic enzymes (e.g., HAS2, HAS3), relaxins, acetylcholine, chitosan, DMSO, N-acetyl-glucosamine, catecholamines, poly unsaturated fats, estrogens and related/derivative molecules, androgens and related molecules, inhibitors of collagen processing (e.g., prolyl 4-hydroylase, C-proteinase and lysyl hydroxylase, HRT peptidases), ZP123, AAP10, rotigaptide, RXP-E and related compounds binding the Cx43 CT, NADPH oxidases, factors effecting connective tissue growth factors (CTGFs), endothelins, and angiotensins, complement proteins, Protein Kinases (e.g., PKC-alpha, PKC-beta, PKC-epsilon, PKC-zeta and other PKC), bioactive fragments or polymers of these molecules (e.g, CT sequences from Protein Kinases), genetic or cellular vectors producing these molecules, binding proteins, molecules targeting the receptors or downstream signal transduction mediators and combinations thereof. As these molecules and their different family members can have opposing effects in different circumstances ligands, agonists (activating factors) and antagonists (or inhibiting factors) of these molecules will be used in the present disclosure.

The polypeptide used with the disclosed tissue engineered invention can be any polypeptide comprising the carboxy-terminal most (CT-most) amino acids of a Connexin, wherein the polypeptide does not comprise the full-length Connexin protein. ACT1 peptide used in one embodiment of the composition is one example of such a CT-most peptide from a connexin.

Connexins are the sub-unit protein of the gap junction channel, which is responsible for intercellular communication (Goodenough and Paul. Nat. Rev Mol Cell Biol. 2003 April; 4(4):285-94, incorporated by reference herein). Connexin channels as well as structurally related molecules can also act as single membrane channels or hemichannels. Connexin molecules can also act as regulatory molecules of signal transduction pathways. In one example, it has been shown that Cx43 can modulate the TGF-beta signaling pathway via a targeting of SMADs, downstream regulators of TGF-beta signaling (Dai et al., Mol Biol Cell. 2007 June; 18(6):2264-73, incorporated by reference herein).

The carboxy-terminus (CT)-most sequence of connexins is a key regulatory domain. For example, the CT-most amino acid sequences of Connexins are characterized by distinct and conserved features. This preservation of structure is consistent with the ability to form characteristics 3D shapes, interact with Cx43 in intra and intermolecular associations, interact with multiple other proteins, interact with lipids and biomembranes, interact with nucleic acids including RNA, transit and/or block membrane channels and provide consensus sequences for proteolytic cleaving, cross-linking, ADP-ribosylation, glycosylation and phosphorylation. Thus, ACT1 interacts with a domain of a protein that normally mediates the binding of said protein to the CT-most sequence of a Connexin. For example, the scaffolding protein ZO-1 interacts with the CT-most domain of Cx43 (Toyofuku et al., J Biol. Chem. 1998 May 22; 273(21):12725-31, incorporated by reference herein). It is considered that this and other proteins interact with the CT-most sequence of Connexins and further interact with other proteins forming a complex of multiple proteins. The polypeptide used with the tissue engineered composition can inhibit the operation of a molecular machine, such as, for example, one involved in regulating the aggregation of Cx43 gap junction channels from hemichannels.

In a further example, nephroblastoma overexpressed protein (NOV) interacts with a Cx43 CT-most domain (Fu et al., J Biol. Chem. 2004 279(35):36943-50, incorporated by reference herein). NOV is a matricellular protein found in the matrix external to cells that has key functions in wound healing. Connexin based peptides thus have assignments that occur outside of the cell or at the external membrane surface of the cell.

In one example defining CT-most connexin peptide there is a conserved proline or glycine residue in Connexins consistently positioned some 17 to 30 amino acids from the carboxyl terminal-most amino acid. For example, for human Cx43 a proline residue at amino acid 363 is positioned 19 amino acids back from the carboxyl terminal most isoleucine. In another example, for chick Cx43 a proline residue at amino acid 362 is positioned 18 amino acids back from the carboxyl terminal-most isoleucine. In another example, for human Cx45 a glycine residue at amino acid 377 is positioned 19 amino acids back from the carboxyl terminal most isoleucine.

In another example for rat Cx33, a proline residue at amino acid 258 is positioned 28 amino acids back from the carboxyl terminal most methionine. The polypeptide used with the disclosed invention can thus comprise the CT-most 4 to 30 amino acids of the Connexin, including the c-terminal most 4, 5, 6, 7, 8, 9, 10, 11, 12, 13, 14, 15, 16, 17, 18, 19, 20, 21, 22, 23, 24, 25, 26, 27, 28, 29, amino acids of the Connexin.

The CT most amino acids of a Connexin can be flanked by non-CT-most amino acids. Examples of the flanking amino acids are provided herein. An example of non-CT-most Connexin amino acids is the carboxy-terminal 20 to 120 amino acids of human Cx43. Another example would be the carboxy-terminal 20 to 120 amino acids of human Cx45. Another example would be the carboxy-terminal 20 to 120 amino acids of chick Cx45. Another example would be the carboxy-terminal 20 to 120 amino of human Cx37. Another example would be the carboxy-terminal 20 to 120 amino acids of rat Cx33.

CT-most peptides retain function when flanked with non-Connexin polypeptides of up to at least 239 amino acids. Indeed, as long as the sequence is maintained as the free carboxy terminus of a given polypeptide, and the peptide is able to access its targets and be able to be used with the present disclosure. Thus, polypeptides exceeding 239 amino acids in addition to the CT-most peptide can function in reducing inflammation, promoting healing, reducing scarring and promoting tissue regeneration in association with the disclosed invention following injury.

The sequence of the polypeptide used with the present disclosure can be from any Connexin. Thus, the Connexin component of the polypeptide can be from a human, murine, bovine, monotrene, marsupial, primate, rodent, cetacean, mammalian, avian, reptilian, amphibian, piscine, chordate, protochordate or other Connexin or conservative variant thereof.

Thus, the provided polypeptide can comprise a component of a Connexin selected from the group including Connexin 47, Connexin 46.6, Connexin 30.2, Connexin 30.2, Connexin 31.9, Connexin 26, Connexin 32, Connexin 44, Rat Connexin 33, Connexin 36, Connexin 37, Connexin 39, Connexin 40.1, Connexin 38, Connexin 39.9, Connexin 40, Connexin 43, Zebrafish Connexin 43, Connexin 43.4, Connexin 44.2, Connexin 44.1, Connexin 45, Connexin 46, Connexin 56, Connexin 39.9, Connexin 49, Connexin 50, Connexin 59, Connexin 32, Connexin 26, or other Connexin. These examples and other amino acid sequences for connexins, structurally related molecules known as pannexins and conservative variants thereof are known in the art.

The 20-30 CT-most amino acid sequence of most Connexins are characterized by a distinctive and conserved organization. This organization can include a class/type II PDZ binding motif ($\Phi$-x-$\Phi$; wherein x=any amino acid and $\Phi$=a Hydrophobic amino acid (aa) and next to this motif, Proline (P) and/or Glycine (G) aas; a high frequency phospho-Serine (S) and/or phospho-Threonine (T) residues; and a high frequency of positively charged Arginine (R), Lysine (K) and negatively charged Aspartic acid (D) or Glutamic acid (E) aas. For many Connexins, the P and G residues occur in clusters next to the CT PDZ binding motif. The S and T phospho-amino acids of many Connexins also are often in clustered, repeating sequences. This organization is the case for Cx43, where 90% of 20 CT-most aas are the latter seven amino acids.

The CT-most peptide of Cx43 is highly conserved from humans to fish (e.g., compare Cx43 sequences for humans and zebrafish). In a further example, CT-most sequence of Cx45 is highly conserved from humans to avians. In yet another example, the sequence of Cx36 is highly conserved from primates to fish Thus, in one aspect, the polypeptide used in association with the present disclosure comprises one, two, three or all of the amino acid motifs selected from the group consisting of 1) a type II PDZ binding motif, 2) Proline (P) and/or Glycine (G) hinge residues; 3) clusters of phospho-Serine (S) and/or phospho-Threonine (T) residues; and 4) a high frequency of positively charged Arginine (R) and Lysine (K) and negatively charged Aspartic acid (D) and/or Glutamic acid (E) amino acids). In another aspect, the provided polypeptide comprises a type II PDZ binding motif at the carboxy-terminus, Proline (P) and/or Glycine (G) hinge residues proximal to the PDZ binding motif, and positively charged residues (K, R, D, E) proximal to the hinge residues.

PDZ domains were originally identified as conserved sequence elements within the postsynaptic density protein PSD95/SAP90, the *Drosophila* tumor suppressor dlg-A, and the tight junction protein ZO-1. Although originally referred to as GLGF or DHR motifs, they are now known by an acronym representing these first three PDZ-containing proteins (PSD95/DLG/ZO-1). These 80-90 amino acid sequences have now been identified in well over 75 proteins and are characteristically expressed in multiple copies within a single protein. Thus, in one aspect, the provided polypeptide can inhibit the binding of a Connexin to a protein comprising a PDZ domain. The PDZ domain is a specific type of protein-interaction module that has a structurally well-defined interaction 'pocket' that can be filled by a PDZ-binding motif, referred to herein as a "PDZ motif". PDZ motifs are consensus sequences that are normally, but not always, located at the extreme intracellular carboxyl terminus Four types of PDZ motifs have been classified: type I (S/T-x-$\Phi$), type II ($\Phi$-x-$\Phi$), type III ($\Psi$-x-$\Psi$) and type IV (D-x-V), where x is any amino acid, $\Phi$ is a hydrophobic residue (V, I, L, A, G, W, C, M, F) and $\Psi$ is a basic, hydrophilic residue (H, R, K). (Songyang, Z., et al. 1997. Science 275, 73-77, incorporated by reference herein). Thus, in one aspect, the polypeptide used with the provided disclosure would comprise a type II PDZ binding motif.

The Cx37 ACT-like sequence is GQKPPSRPSSSASKKQ*YV. Thus the carboxy terminal 4 amino acids of Cx37 conform only in part to a type II PDZ binding domain. Instead of a classical type II PDZ binding domain, Cx37 has a neutral Q* at position 2 where a hydrophobic amino acid would be expected. As such Cx37 comprises what can be termed a type II PDZ binding domain—like sequence. Nonetheless, Cx37 strictly maintains all other aspects of peptide organization including clustered serine residues, frequent R and K residues and a P-rich sequence proximal to the PDZ binding domain-like sequence. Given this overall level of conservation of ACT-like organization in common with the other >70 Connexins described herein, it is understood that the Cx37 CT functions in the provided capacity in the disclosure described herein.

The Connexin Cx26 has no carboxyl terminal type II PDZ binding motif; about 30% of the carboxyl terminal most amino acids comprise S, T, R, D or E residues; it has no evidence of motifs proximal to a type II PDZ binding motif or PDZ binding like motif containing clusters of P and G hinge residues; and no evidence of clustered, repeat-like motifs of serine and threonine phospho-amino acids. Cx26 does have three Lysine (K) residues, clustered one after the other near the carboxy terminus of the sequence.

As herein provided with the present disclosure, the unique functional characteristics of this relatively short stretch of amino acids encompass unexpected roles in reducing inflammation, promoting healing, reducing scarring and promoting regeneration of complex tissue structure and function following injury in tissues as diverse as skin and brain. Thus, in one aspect, the provided polypeptide comprises a type II PDZ binding motif (Φ-x-Φ; wherein x=any amino acid and Φ=a Hydrophobic amino acid). In another aspect, greater than 40%, 50%, 60%, 70%, 80%, 90% of the amino acids of the provided polypeptide is comprised one or more of Proline (P), Glycine (G), phospho-Serine (S), phospho-Threonine (T), Arginine (R), Lysine (K), Aspartic acid (D), or Glutamic acid (E) amino acid residues.

The amino acids Proline (P), Glycine (G), Arginine (R), Lysine (K), Aspartic acid (D), and Glutamic acid (E) are necessary determinants of protein structure and function. Proline and Glycine residues provide for tight turns in the 3D structure of proteins, enabling the generation of folded conformations of the polypeptide required for function. Charged amino acid sequences are often located at the surface of folded proteins and are necessary for chemical interactions mediated by the polypeptide including protein-protein interactions, protein-lipid interactions, enzyme-substrate interactions and protein-nucleic acid interactions. Thus, in another aspect Proline (P) and Glycine (G) Lysine (K), Aspartic acid (D), and Glutamic acid (E) rich regions proximal to the type II PDZ binding motif provide for properties necessary to the actions of peptides in association with the present disclosure. In another aspect, the polypeptide comprises Proline (P) and Glycine (G) Lysine (K), Aspartic acid (D), and/or Glutamic acid (E) rich regions proximal to the type II PDZ binding motif.

Peptides, peptide mimetics or conservative variants can be made to modulate gap junction, hemichannel or other independent biological functions in association with the present disclosure that are based on the amino-terminal, extracellular, cytoplasm loop and transmembrane domains of connexin family members can also be used to develop peptide gap junction, hemichannel of connexin based signal transduction modulating agents. Such peptides can comprise from ~3 to ~30, for example a 14 amino acid long sequence, or from ~6 to ~15 amino contiguous amino acids of sequence, for example a 6 amino acid long sequence. In a further example, Cx43 mimetic peptidergic inhibitors of Cx43-based gap junction communication that can be used with the present disclosure include:

FEVAFLLIQWI, LLIQWYIGFSL, SLSAVYTCKRDPCPHQ E2,

VDCFLSRPTEKT, SRPTEKTIFII, LGTAVESAWGDEQ, QSAFRCNTQQPG,

QQPGCENVCYDK E1, VCYDKSFPISHVR E1.

Related sequences incorporating the extracellular loop domains that modulate gap junction, hemichannel or other independent biological functions can be found for all other connexin family members connexins including Cx45, Cx40, Cx32, Cx26, Cx31 and all other known connexins and pannexins by those skilled in the art.

Genetic vectors (e.g., transfected cDNA, viral vectors and the like) expressing these sequences listed above or combinations of other factors with said vectors and peptides are also contemplated to be used in association with the provided disclosure.

Phosphorylation is the most common post-translational modification of proteins and is crucial for modulating or modifying protein structure and function. In one example Cx43 is phosphorylated at the serine residue 368 (s368). Phosphorylation at s368 is associated with preconditioning of the myocardium. Phosphorylation at s368 causes changes in permselectivity of the Cx43 gap junction channel and hemichannels. Phosphorylation at s368 can promote communication compartments in tissues that inhibits spread of cell and tissue damage into otherwise normal tissues adjacent to an injury. ACT1 can promote phosphorylation at s368. Aspects of protein structure and function modified by phosphorylation include protein conformation, protein-protein interactions, protein-lipid interactions, enzymatic function, protein-nucleic acid interactions, channel gating, protein trafficking and protein turnover. Thus, in one aspect the phospho-Serine (S) and/or phospho-Threonine (T) rich sequences are necessary for modifying the function of the molecules, increasing or decreasing efficacy of the polypeptides in their actions. In another aspect, the provided polypeptide comprise Serine (S) and/or phospho-Threonine (T) rich sequences or motifs. Exemplary phosphorylating agents are well known in the art and can include, TPA, Src or G protein-coupled receptor antagonists and agonists. Phosphorylation and dephosphorylation to inhibit, enhance or otherwise modify the activity of molecules used for the purpose of the present disclosure are thus contemplated.

When specific proteins are referred to herein, variants, derivatives, and fragments are contemplated to be used with the present disclosure. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues, but can occur at a number of different locations at once; insertions usually will be on the order of about from 1 to 10 amino acid residues. Deletions or insertions preferably are made in adjacent pairs, i.e., a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place. Such substitutions generally are referred to as conservative substitutions.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations. Conservatively substituted variations of each explicitly disclosed sequence are included within the polypeptides provided herein.

Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Further information about conservative substitutions can be found in, among other locations, in Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), all of which are incorporated by reference herein, and in standard textbooks of genetics and molecular biology.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, substition of seryl or threonyl residues with glutamyl and asparyl residues, methylation of the o-amino groups of lysine, arginine, and histidine side chains (T. E. Creighton, Proteins: Structure and Molecular Properties, W.H. Freeman & Co., San Francisco pp 79-86 [1983], incorporated by reference herein), acetylation of the N-terminal amine and, in some instances, amidation of the carboxyl-terminal.

It is understood that there are numerous amino acid and peptide analogs, which can be incorporated into the disclosed compositions. For example, there are numerous D amino acids or amino acids which have different substituents. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994), all of which are herein incorporated by reference at least for material related to amino acid analogs).

Molecules can be produced that resemble polypeptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such (Such as what). Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Thus, for example, in the case of CT-most polypeptides, these sequences can comprise a conservative variant. An example of a single conservative substitution within the sequence RPRPDDLEI is given in the sequence RPRPDLEV. An example of three conservative substitutions within the sequence RPRPDDLEV is given in the sequence RPRPDDVPV. Thus, the provided polypeptide can comprise aa sequences.

It is understood that one way to define any variants, modifications, or derivatives of the disclosed genes and proteins herein is through defining the variants, modification, and derivatives in terms of sequence identity (also referred to herein as homology) to specific known sequences. Specifically disclosed are variants of the nucleic acids and polypeptides herein disclosed which have at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to the stated or known sequence. Those of skill in the art readily understand how to determine the sequence identity of two proteins or nucleic acids. For example, the sequence identity can be calculated after aligning the two sequences so that the sequence identity is at its highest level.

Another way of calculating sequence identity can be performed by published algorithms. Optimal alignment of sequences for comparison can be conducted by the local sequence identity algorithm of Smith and Waterman Adv. Appl. Math. 2: 482 (1981), by the sequence identity alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference in their entirety for the methods of calculating sequence identity.

The same types of sequence identity can be obtained for nucleic acids by, for example, the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989, which are herein incorporated by, reference for at least material related to nucleic acid alignment.

Other non-peptidergic modulating agents that can be used in association with the present disclosure include, Fatty acids; oleic acid, arachidonic acid, and lipoxygenase metabolites; aliphatic alcohols; heptanol, octanol anesthetics; halothane, propofol, ethflurane, and thiopental; anandamide; arylaminobenzoate (FFA: flufenamic acid and lipophilic derivatives); 2',5'-dihydroxychalcone; Chlorohydroxyfuranones; 3-chloro-4-chloromethyl-5-hydroxy-2(5H)-furanone; dexamethasone; doxorubicin (and derivatives); eicosanoid thromboxane A(2) (TXA(2)) mimetics; nitric oxide; Fenamates; Genistein; glycyrrhetinic acid (GA):18a-glycyrrhetinic acid and 18-beta-glycyrrhetinic acid, and derivatives thereof; lysophosphatidic acid; lindane; mefloquine; menadione; 2-Methyl-1,4-naphthoquinone, vitamin K(3); nafenopin; okadaic acid; oleamide; PH, gating by intracellular acidification; e.g. acidifying agents; polyunsaturated fatty acids; quinidine; quinine; all trans-retinoic acid; vitamin A and retinoic acid derivatives and tamoxifen.

Modulation of gap junctional intercellular coupling or between extracellular and the intercellular space by connexin/pannexin hemichannels, and effects of connexin domains on signal transduction and enzymatic pathways, chaperoning and transport of molecules, and effects on ECM molecular and cellular organization are within the scope of certain compounds and embodiments that will be used in the present disclosure.

It is contemplated that the aforementioned structures, including those of different size, shape regularity and cellular composition, can be combined to generate organ-like structures of complex shape, size and internal structure, as illustrated in FIG. 4b. It is also understood that the manufacture contemplated can involve an iterative mechanism that is capable of combining stacks of the forementioned structures to build up increasing complexity of shape in sequential and repeatable manner. The structures generated can be used as scaffolds upon which to build further complexity via addition of one or more cell types, matrix molecules and other additives that enable the accretion of further biological complexity upon the initial contractile scaffold.

The present disclosure can also assist in the healing of normal wounds, including those resulting from accidents, surgery or failure of healing of a surgical wound (e.g., a dehiscent wound).

For example, the certain aspects of the present disclosure will modulate cell migration and proliferation, thereby reducing inflammation, accelerating wound healing, reduce scarring and ultimately promote repair, regeneration and restoration of structure and function in all tissues. The reduction in inflammation will speed-up wound closure and consequently the process of wound healing. Healing of wounds, post-peptide application will involve significantly reduced fibrosis, consequently reduced scarring in skin wounds and fibrous patches in internal tissue injuries, promoting tissue regeneration and restoring tissue and organ structure and function.

Further, the invented tissue engineered composition can be used to treat external wounds caused by, but not limited to scrapes, cuts, lacerated wounds, bite wounds, bullet wounds, stab wounds, burn wounds, sun burns, chemical burns, surgical wounds, bed sores, radiation injuries, all kinds of acute and chronic wounds, wounds or lesions created by cosmetic skin procedures and also ameliorate the effects of skin aging. The actions of the present disclosure will accelerate wound healing in all kinds of external wounds and improve the cosmetic appearance of wounded areas, and skin subject to aging and disease. The disclosed invention may be provided directly, as a pre-treatment, as a pre-conditioning, coincident with injury, pre-injury or post-injury. The composition be used to treat internal injury caused by, but not limited to, disease, surgery, gunshots, stabbing, accidents, infarcts, ischemic injuries, to organs and tissues including but not limited to heart, bone, brain, spinal cord, retina, peripheral nerves and other tissues and organs commonly subject to acute and chronic injury, disease, congenital and developmental malformation and aging processes. Injury to internal organs causes a fibrotic response, which leads to loss of structure and function in organ systems. In central nervous system (CNS) this response to injury is mediated by astrocytes (fibroblast-like cells in the CNS) and thus will subsequently be referred to as an astrocytic response. Embodiments of the present disclosure will alleviate this fibrotic/astrocytic response hence helping in repair and regeneration of injured tissues and restoration of tissue and organ structure and function.

Regenerative processes aided by the tissue engineered composition include, but are not limited to internal and external injury, regeneration of tissues, organs, or other body parts, healing and restoration of function following vascular occlusion and ischemia, brain stroke, myocardial infarction, spinal cord damage, brain damage, peripheral nerve damage, ocular damage (e.g., to corneal tissue), bone damage and other insults to tissues causing destruction, damage or otherwise resulting from, but not limited to, injury, surgery, cancer, congenital and developmental malformation, and diseases causing progressive loss of tissue structure and function, including but not limited to diabetes, bacterial, viral and prion-associated diseases, Alzheimer's disease, Parkinson's disease, AIDs and other genetically determined, environmentally determined or idiopathic disease processes causing loss of tissue/organ/body part structure and function. In addition, the compositions described herein can be administered with drugs or other compounds promoting tissue and cellular regeneration including, but not limited to, trophic factors in processes including, but not limited to, brain, retina, spinal cord and peripheral nervous system regeneration (e.g., NGFs, FGFs, Neurtrophins, Neuregulins, Endothelins, GDNFs, BDNF. BMPs, TGFs, Wnts), as well as pre-conditioning factors or stimuli e.g., hypoxia, norepinephrine, bradykinin, anesthetics, nitrate, ethanol, Alda-1, ALDH2 antagonists, PKC-epsilon agonists, exogenous ligands that activate opioid receptors (DPDPE, deltorphin II, methadone, SNC-80, BW373U86, DPI-287, DPI-3290) delivered in a prospective pre-treatment prior to a surgery of other procedure disrupting tissue in a subject.

A further embodiment of the present disclosure comprises the use of tissue engineered compositions to alleviate the symptoms of Multiple Sclerosis (MS). MS is a chronic disease of the central nervous system. Pathologically, MS is characterized by the presence of areas of demyelination and T-cell predominant perivascular inflammation in the brain white matter. The anti-inflammatory and regenerative properties of the treatment will help in the treatment of MS and other conditions similar to it.

The compositions of the present disclosure will help with conditions like, but not limited to psoriasis, scleroderma, acne, eczema and other diseases of skin and connective tissues. Psoriasis, a chronic, inflammatory skin disease characterized by an uncontrolled shedding of the skin and afflicts millions of people throughout the world. The effects of the treatment on fibroblasts and inflammatory response of the treatments, as stated in the claims above, will help alleviate Psoriasis. Eczema is characterized by painful swelling, oozing of the skin, bleeding cracks, severe scaling, itching and burning. As stated above, the effects of the treatment on fibroblasts and inflammatory response, combined with accelerated healing properties will relieve symptoms of eczema.

Said tissue engineered compositions will help with repair after cosmetic and/or clinical procedures involving, but not limited to, controlled damage—e.g., corneal laser surgery, laser and dermabrasion/dermaplaning, skin resurfacing, and punch excision. Application of the treatment immediately after surgery or any cosmetic procedure will reduce or eliminate scarring. Uses of said composition will reduce keloid scar formation. Keloid scars are common in dark skin people of Asian, African, or Middle Eastern descent. Keloid scar is a thick, hypertrophic puckered, itchy cluster of scar tissue that grows beyond the edges of a wound or incision. Keloid scars are sometimes very nodular in nature, and they are often darker in color than surrounding skin. They occur when the body continues to produce tough, fibrous protein (known as collagen) after a wound has healed. Application of the treatment will ameliorate formation of Keloid or hypertrophic scars.

Additional uses of the tissue engineered compositions of the present disclosure will help correct other diseases and other conditions (e.g., congenital and developmental defects, aging) associated with inflammatory response, fibrosis and connective tissue disorders. Fibrosis is a common condition noted after trauma to any bodily organ or tissue. Excessive fibrosis results in loss of structure and function and scarring at the trauma site. The treatment will reduce fibrosis and promote regeneration, and restoration of structure and function.

Said compositions will modulate cell proliferation and can be used alone or in association with drugs used in the treatment of uncontrolled proliferation (e.g., anti-cancer drugs) and procedures (e.g., radiation therapy). Diseases of uncontrolled cell proliferation, or hyperplasias, are common health problems. Examples of diseases of cell over-proliferation include but are not limited to psoriasis, seborrhea, scleroderma, eczema, benign prostate hyperplasia, congenital adrenal hyperplasia, endometrial hyperplasia, squamous cell (vulvular) hyperplasia, sebaceous hyperplasia, Crohn's Disease, leukemia, carcinoma, sarcoma, glioma, and lymphoma. The compositions described herein limit undesirable cellular proliferation and will thus improve prognosis of conditions associated with excessive cell proliferation.

The compositions of the present disclosure will have effects on cell migration, proliferation and differentiation and thus will assist in preventing metastasis. The compositions can be administered alone or in association with drugs or procedures used in the treatment of metastasis like but not limited to, Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine. Metastasis is the spread of cancer from its primary site to other places in the body. Cell migration is the movement of cells from one part of the body to another. The treatments of the present disclosure can effect cell migration which demonstrates an ability to inhibit spread of tumors.

Additional embodiments of the present disclosure comprise the use of the compositions in vitro and/or in animal models humanized or otherwise to promote and/or assist in the regeneration of tissues, organs and body parts for use, but not limited to organ/tissue or body part transplantation.

Examples of medical uses of the present disclosure include healing of pathological wounds, such as through use of a contractile toroid for assisting the closure of slow healing wounds e.g., diabetic wounds as shown in FIG. 5b.

Diabetic wounds are examples of difficult to heal wound can include, for example, a wound that is often characterized by slower than normal re-epithelialization/closure inflammatory phase and delayed formation and remodeling of extracellular matrix.

The present disclosure can also assist in the healing of chronic wounds or wounds that do not heal. Wounds that have not healed within three months, for example, are said to be chronic. Chronic wounds include, diabetic, diabetic foot, ischemic, venous, venous stasis, arterial, pressure, vasculitic, infectious, decubitis, burn, trauma-induced, gangrenous and mixed ulcers.

Chronic wounds include, wounds that are characterized by and/or chronic inflammation, deficient and overprofuse granulation tissue differentiation and failure of re-epithelialization and wound closure and longer repair times.

Chronic wounds can include ocular ulcers, including corneal ulcers. Use of the disclosed invention in would healing and tissue regeneration would include in humans and agricultural, sports and pet animals.

The present disclosure contemplates that the regenerative effects of the tissue engineered composition will include beneficial changes in membrane excitability and ion transients of the heart, nervous system, uterus and other tissues in health and disease There are many different types of arrhythmia that can lead to abnormal function in the human heart. All forms of arrhythmia have associated morbidity and can have the potential to result in sudden cardiac death (SCD). Tachyarrhythmias, like ventricular tachycardia and ventricular fibrillation are the predominant mechanisms leading to SCD. In the clinic, SCD is most commonly linked to coronary artery disease and subsequent transient ischemia. These episodes of transient ischemia can induce gap junction remodeling in un-injured tissues, and this remodeling can then cause arrhythmia.

Common arrhythmias include bradycardias, tachycardias, automaticity defects, reentrant arrhythmias, fibrillation, AV nodal arrhythmias, atrial arrhythmias and triggered beats. It is anticipated that the said composition, in addition its use in regenerative restoration of heart structures will be used to treat cardiac rhythm disturbances of these types.

There are many diseases of congenital, genetic and acquired origins that manifest as a primarily electrical pathophysiology. In such cases accompanying tissue injury is not a factor in the generation of the arrhythmogenic substrate. These include, but are not limited to, Long QT syndrome, Short QT syndrome, Brugada syndrome, and several accessory pathway disorders. One example, Wolff-Parkinson-White syndrome (WPW) is a condition where an accessory bundle of muscle, expressing electrical connection, links the atrium and the ventricle of the subject. This additional pathway provides the substrate for a reentrant circuit between the atrium and the ventricle which when activated can result in ventricular tachycardia, and potentially lead to SCD. The present disclosure contemplates that treatment of the subject with the tissue engineered composition will modulate the likelihood of this reentrant pathway to become activated. It is further contemplated that this effect will be the result of the compositions modulation of membrane excitability in the region of reentrant activity.

Arrhythmias can also be the result of molecular abnormalities in the working myocardium. These molecular abnormalities can be caused by the cellular response to environmental stress, genetic mutations, infection, and other conditions. One example of this type of disease is Hypertrophic Cardiomyopathy (HCM). HCM is the number one cause of sudden cardiac death in patients under 30 years of age. This disease can be transmitted genetically and results in the unchecked growth of the myocardium without any signs of injury. It can be diagnosed with a preventative physical exam and/or thorough family history. In this condition, gap junction remodeling in the hypertrophic working myocardium leads to the increased incidence of arrhythmia and can cause SCD. This outcome is often seen as the otherwise healthy young person who suddenly dies after a period of exercise. Examples of such subjects occasionally can be seen in media stories concerning young prominent athletes who die suddenly of an unexpected heart attack. The present disclosure contemplates that treatment with the provided compositions will prevent the occurrence of unexpected arrhythmias in these subjects.

Other common arrhythmias include premature atrial Contractions, wandering Atrial pacemaker, Multifocal atrial tachycardia, Atrial flutter, Atrial fibrillation, Supraventricular tachycardia, AV nodal reentrant tachycardia is the most common cause of Paroxysmal Supra-ventricular Tachycardia, Junctional rhythm, Junctional tachycardia, Premature junctional complex, Wolff-Parkinson-White syndrome, Lown-Ganong-Levine syndrome, Premature Ventricular Contractions (PVC) sometimes called Ventricular Extra Beats, Accelerated idioventricular rhythm, Monomorphic Ventricular tachycardia, Polymorphic ventricular tachycardia, Ventricular fibrillation, First degree heart block, which manifests as PR prolongation, Second degree heart block, Type 1 Second degree heart block, Type 2 Second degree heart block, Third degree heart block. It is anticipated that the compositions of the present disclosure can be used to treat cardiac rhythm disturbances of these types.

Common drugs used for arrhythmia treatments include class Ia drugs e.g., Quinidine, Procainamide, Disopyramide, class Ib drugs e.g., Lidocaine, Phenyloin, Mexiletine, class Ic drugs e.g., Flecamide, Propafenone, Moricizine, class II drugs e.g., Propranolol, Esmolol, Timolol, Metoprolol and Atenolol, class III drugs e.g., Amiodarone, Sotalol, Ibutilide and Dofetilide, class IV drugs e.g., Verapamil, Diltiazem and class V drugs e.g., Adenosine and Digoxin. The present disclosure anticipates that TGF-beta3, ACT1 or other components described herein in the provided compositions can be used in conjunction with these approaches to treatment of arrhythmia.

Other arrhythmia treatments include: Anticoagulant therapies, electrical treatments, electrical cautery, cryo-ablation, radio frequency ablation, implantable cardioverter-defibrillator, and implantable pacemaker. The present disclosure anticipates that the compositions can be used in association with these approaches for the treatment of arrhythmia.

Epilepsy is a chronic neurological disorder characterized by recurrent, transient, unprovoked seizures, resulting from disturbed neuronal activity in the brain. There is evidence that epilepsy is caused by dysregulated connexin coupling between neuronal cells and disturbances to Cx43 have been noted in human hippocampus associated with severe epilepsy. Over 50 million people worldwide have epilepsy. Over 30% of people with epilepsy do not respond to currently available medications. The uncontrolled electrical disturbance associated with epilepsy often leads to comparisons to cardiac arrhythmias.

Common forms of epilepsy include: Autosomal dominant nocturnal frontal lobe epilepsy, Benign centrotemporal lobe epilepsy of childhood, Benign occipital epilepsy of childhood, Catamenial epilepsy, Childhood absence epilepsy, Dravet's syndrome, Frontal lobe epilepsy, Juvenile absence epilepsy, Juvenile myoclonic epilepsy, Lennox-Gastaut syndrome, Primary reading epilepsy, Progressive myoclonic epilepsies, Rasmussen's encephalitis, Symptomatic localization-related epilepsies, Temporal lobe epilepsy, West syndrome. The present disclosure anticipates that the tissue engineered compositions described herein can be used to treat these epilepsies.

The following medications are used for treatment of epilepsy: carbamazepine, clorazepate (Tranxene) clonazepam (Klonopin), ethosuximide (Zarontin), felbamate (Felbatol), fosphenyloin (Cerebyx), gabapentin (Neurontin), lamotrigine (Lamictal), levetiracetam (Keppra), oxcarbazepine (Trileptal), phenobarbital (Luminal), phenyloin (Dilantin), pregabalin (Lyrica), primidone (Mysoline), tiagabine (Gabitril), topiramate (Topamax), valproate semisodium (Depakote), valproic acid (Depakene), zonisamide (Zonegran), clobazam (Frisium) and vigabatrin (Sabril), retigabine, brivaracetam, and seletracetam, diazepam (Valium, Diastat) and lorazepam (Ativan), Paral, midazolam (Versed), and pentobarbital (Nembutal), acetazolamide (Diamox), progesterone, adrenocorticotropic hormone (ACTH, Acthar), various corticotropic steroid hormones (prednisone), or bromide. The present disclosure anticipates that the compositions described herein can be used in association with these drugs in treatment of epilepsy.

Other epilepsy treatments include: ketogenic diet, electrical stimulation, vagus nerve stimulation, responsive neurostimulator system (rns), deep brain stimulation, invasive or noninvasive surgery, avoidance therapy, warning systems, alternative or complementary medicine. It is anticipated that the compositions can be used in association with these approaches to treatment of epilepsy.

The modulatory agents listed herein can be given in association with the present disclosure, such as described herein as a therapy or medicament to improve the healing of wounds, injuries, disease processes, surgeries, congenital malformations and regenerating tissue in a subject. In summary, EMT-priming will be useful in all manner of medical treatments involving cellular therapy to synchronize the healing and/or regenerative capacity of engrafted cells.

The agent can be formulated with a pharmaceutically acceptable carrier to provide the desired final concentration for site-specific, transient or systemic effect in association with the present disclosure.

The modulating agent can be present in direct association with the tissue engineered device or present in a substantially isolated form; a state that will not change following mixing with carriers or diluents.

The modulatory agent can be administered integral with the tissue engineered construct. In this case the provided agent will be dissolved in solution within the solution of the hydrogel or can be present as particles, nano-particles or some other vector that releases the agent into the healing tissue. The agent can also chemically bonded to the molecules of hydrogel itself. The hydrogel will contain ~001% to about 1.5% of active ingredient(s), about 2%-60% of active ingredient(s), ~2%-70% of active ingredient(s), or up to ~90% of active ingredient(s).

The agent provided as part of the present disclosure can also be delivered in a substantially isolated form independent of the tissue engineered composition. The route of delivery, compositions, preparations and medicaments of the present disclosure can be in gels, oils, foams, sprays, ointments, suspensions, instillations, salves, creams, solutions, emulsions, lotions, paints, sustained release formulations, or powders, and typically contain active concentrations that will be the same as those listed above for integral administration.

The modulating agents delivered as part of the present disclosure can also be combined with a pharmaceutically acceptable carrier or diluent to provide a pharmaceutical composition. Suitable for this are isotonic saline solutions, water, saline, dextrose, glycerol, or the like, and combinations thereof. In addition substances such as emulsifying agents, stabilizing or ph buffering agents can be present.

The factors used in association with the tissue engineered device can be administered topically, orally, or parenterally. For example, the compositions can be administered extracorporeally, intracranially, intravaginally, ophthalmically intraanally, rectally, subcutaneously, intradermally, intracardiac, intragastric, intravenously, intramuscularly, by intraperitoneal injection, transdermally, intranasally, or by inhalant. As used herein, "intracranial administration" means the direct delivery of substances to the brain including, for example, intrathecal, intracisternal, intraventricular or transsphenoidal delivery via catheter, needle or intravenous drip.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels (e.g., poloxamer gel), drops, suppositories, sprays, liquids and powders. Conventional pharmaceutical carriers, aqueous, powder or oily bases, thickeners and the like can be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or all bio-engineered materials.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the compositions can be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual doctor in the event of any counter indications. Dosage can vary, and can be administered in one or more dose administrations daily, for one or several days. Guidance can be found in the literature for appropriate dosages for given classes of pharmaceutical products.

The dose effective provided with the tissue engineered compositions of the present disclosure for a given subject or wound can be determined by experimenting via methods known to those skilled in the art or developed by experimentation by those skilled in the art using culture, animal models and other biomedical approaches. Therapeutically effective doses are those that render therapeutic benefit in at least 50% of the population, and that show minimal, low or no toxicity at the effective dose. Other factors such as the route of administration, frequency of administration, and patient age, sex, weight, health, disease-profile, and other relevant medical information, the wound exhibited by the subject and the modulating agent that is being used will be also used to calculate effective dose. For example depending on the size of the wound treated and scale of the tissue engineered composition dose can have to be adjusted accordingly. Different active agents can be delivered together or separately, and simultaneously or at different times within the day. The doses can be administered in single or divided applications and given at repeat intervals over a time course beneficial to the subject or suitable for the therapeutic use at hand. Co-treatment or pre-treatment localizing co-factors (e.g., TGF-3B3 or ACT1) at the site of injury (e.g., in a gel directly adherent to an MI) or disease can be particularly effective alone or in combination with the provided invention.

A suitable dose given with the tissue engineered composition can be based on the mass of modulating agent per kg of body weight of the patient, and include, from 0.00002 to about 200 mg/kg body weight e.g., 0.002 to about 50 mg/kg body weight. A suitable dose can however be from ~0.0002 to 0.2 mg/kg body weight e.g., 0.002 to about 0.060 mg/kg body weight. Doses from ~1 to 100, 200, 300, 400, 500, 1000, 2000 micrograms per administration are appropriate. In certain embodiments, modulating agent composition can be used at ~0.0001 micromolar (µM) or 0.06 µM to about 300 µM, or up to 500 µM or up to 1500 µM, or up to 3000 µM or up to 4200 µM or more, final concentration at the treatment site and/or adjacent to the treatment site, and any doses and dose ranges within these dose numbers.

The skin provides a model of scar reduction/regenerative healing effects. However, the present disclosure contemplates toroidal or other morphogenetically induced constructs being of use in the regenerative repair and scar reduction in various tissues and organs including the skin, heart, brain, spinal cord and eye. The contemplated benefits would apply following injury, surgery, medication, chronic or acute disease, malformation and other normal or pathological processes causing loss of tissue structure and function, pathology and/or replacement with scar tissue.

For instance, surgical repair of congenital structural defects can take place through use of contractile toroids in utero for assisting in closure of defects in embryos such as ventricular septal defects of the heart. In regenerative medicine, the compositions and methods of the present disclosure can be utilized for a scaffold for tissue-engineered circularized muscular structures, such as synthetic venous valves or bladder sphincter valves. A further use in regenerative medicine is as a building block for tissue engineering complexes that are mechanically active or responsive biological structures. Specific examples of this can include branched and unbranched tubular structures such as synthetic blood vessels (as shown in FIG. 5b), aortic and pulmonary vessels, glandular ducts, lymphatic vessels, sinuses, lung bronchi and bronchioles, digestive tract, urethra, reproductive tubes and the like. Further examples can include the combination of regular and irregular toroids to generate hollow organs or organ substructures such as bladders, gall bladders, gastrointestinal tract, pancreas lung air sacs, kidney nephrons and the like.

Previously described herein is the disclosure of novel compositions generated in vitro (e.g., toroidal rings of cells). The induction of these compositions is via a novel method that recapitulates embryonic-like morphogenetic processes in vitro similar to those that occur as a prelude to the generation of natural complexities of tissue structure, function, and signaling in vivo. The novel compositions and methods described herein represent transformative technologies in wound healing, greatly enhancing the performance of a number of other wound healing therapies. Current therapies based on stem cells usually involve the introduction of dispersed cells into a diseased organ with little regard for the synchronization and activation of the potentiality of these cells for regenerative repair. Here, evidence is provided that this present widely used approach of randomly introducing stem cells can not be effective, perhaps even deleterious. Only when stem cells were primed in the culture dish using the present methods prior to engraftment into a wound was there a subsequent dramatic improvement in the regenerative healing of the treated animal. The new principles outlined in this disclosure have the potential to revolutionize the standard care for cell-based therapies of injuries or any therapeutic approach in which stem cells are used as a therapy for patients.

The present disclosure can be better understood with reference to the following examples.

EXAMPLES

In the present example, a novel method is described for harnessing EMT to generate repeatable and geometrically distinct microtissue units, including contractile rings and hollow spheroids. The standard protocol for gel contraction involves premixing cells into a collagen suspension, allowing the collagen-cell mixture to polymerize as a 4 mm thick gel at the bottom of a the circular well of a multi-well plate, detaching the gel after a period of culture and then measuring the amount that the composite contracts. Typical results for the contraction assay are shown in FIG. 1a, where following detachment the gel is contracted by cells showing varying degrees of heterogeneous and mostly unorganized dispersion in the circular three-dimensional matrix.

In a variation on this protocol, cells were added onto an already polymerized gel and the gel was detached after 24 hours of culture. Following a subsequent 24 hours it was noted that quite unlike what was observed when cells were pre-mixed into the gel, cells added post-polymerization always formed into uniform circular rings of repeatable diameter (FIG. 1b). It was also found that ring size can be predictably altered by either undertaking the culture in a circular well of smaller diameter (FIG. 1c) or by addition to the culture fluid of 3-30 ng TGF-b, a well known inducer of the EMT (FIG. 1d). Confocal microscopy of rhodamine-phalloidin and nuclear-DAPI stained gels indicated a two-phase structure with cells undergoing recruitment at the outer rim arranging in radial spoke-like arrays (FIG. 1e), whereas cells in on the inner rim organized into a contractile ring (FIG. 1f). Biomechanical measurements undertaken on gels indicated that the toroidal units efficiently exerted force on the gel that exceeded that of pre-mixed gel-cell composites (mean, se, t-test). The results indicated that by actively forcing the cells to undergo a round of EMT during invasion of the poymerized collagen gel, a morphogenetic event had been initialized that led to self-organization of the mesencyhmal cells into a contractile ring. This experiment was repeated with REC cells (Wada A M, Smith T K, Osler M E, Reese D E, Bader D M. Epicardial/Mesothelial cell line retains vasculogenic potential of embryonic epicardium. Circ Res. 2003 Mar. 21; 92(5): 525-31. Epub 2003 Feb. 6, incorporated by reference herein), a rat embryonic stem cell line with similar effect. REC progenitor cells also organized into a distinct ring in the hydrogel when seeded onto the top of the gel and the then detached. These higher order toroidal structures failed to materialize for all cell types tested including BMSCs and embryonic stem cells if the cells were passively mixed into a liquid gel and allowed to set in situ.

Further analysis revealed the result if the shape of the gel was varied. 2 mm thick collagen gels were thus polymerized in square wells. As was the case with circular wells, when cells were pre-mixed into the gel, following detachment square gels contracted, but showed nothing distinctive about the dispersion or organization of the gel-cell composite over a 48 hour time course (FIG. 4b). However, square gels to which cells had been added post-polymerization consistently formed into three-dimensional spheroids of uniform shape and size with a single apical pore after 48 hours of culture (FIG. 4a). These spheroidal units can be filled with FITC dye via the pore and did not leak dye except at the pore mouth, indicating that the spheroids were hollow and relatively well sealed structures. Tracking over time suggested a step-wise process, by which cells initially formed a star-like arrangement that concavely deformed the gel edges, then progressively folded the apices of the square upwards to form the spheroid with its apical pore.

Formation of contractile rings or so-called actin purse strings is a process commonly found in biology (Martin A C, Kaschube M, Wieschaus E F. Pulsed contractions of an actin-myosin network drive apical constriction. *Nature*. 2008 Nov. 23; incorporated by reference herein). For example, contractile rings have been observed in neuropore closure in *Drosophila* and also elaborate to effect wound closure in mammalian embryos (Martin P, Lewis J. Actin cables and epidermal movement in embryonic wound healing. *Nature*. 1992 Nov. 12; 360(6400):179-83; incorporated by reference herein). Tissue-engineered contractile rings can have uses in promoting wound closure (e.g., slow healing diabetic ulcers) or in repair of congenital malformations such as closing septal defects in the heart. A further potential application of self-organized toroids and spheroids is as microtissue units or building blocks for more complex biological structures, perhaps in combination with organ printing technologies. For example, it can be envisaged that contractile toroids can be iteratively stacked to build a branched tubular structure resembling a blood vessel. In conclusion, the present example describes a method for generation of unitary microtissues based on the harnessing of self-organizing, morphogenetic processes. These microtissue units can provide a basis for incorporation and elaboration of naturally occurring histo-complexity and function found in living organisms into artificially engineered tissues.

Examples from Skin

In the next example, stem cells were primed using the method described herein prior to engraftment into a wound. Adult bone marrow stromal cells (BMSC) were isolated from adult rat femurs and passaged and cultured to produce a pure population of BMSC. A small biopsy punch (8 mm) was used to create a small, 8 mm diameter round wound on the back of the animal. The punch site was inlayed with the preformed collagen cell containing the BMSC cells (toroid) and/or peptide and two 4-0 prolene stitches were placed in the skin at the biopsy sight to hold the gel in place. The collagen gel (1 mg/ml) was polymerized in a sterile hood and BMSC cells were treated with the ACT1 peptide (150 uM) and then added either on top of the 1.5 mm gel (toroid) or mixed into the polymerizing gel. Wounds were also treated with the gel only, gel plus ACT1 alone, gel plus cells alone and toroids with a control peptide. Animals were allowed to heal for 30 days and then sacrificed and the pelts were removed and the wounds excised and surrounding skin were processed for standard embedding in paraffin epidermal surface-up. From wound edge to wound edge every 30th section was mounted on a glass slide and stained with H&E histochemistry. Images of the granulation in each section were then recorded as single images or montages of 2-3 images. Generally 15-30 serial 300 um-spaced sections were recorded per wound. The granulation tissue area, length of epidermal surface and number of follicles intersecting the epidermis were then counted or measured using Image J software from each wound montage. Estimates of wound granulation tissue volume and the granulation tissue area measurements were recorded for each section. Similarly, scar surface area was estimated as was follicle density in the scar epidermis. T-tests for paired samples were carried using MS Excel (p<0.05). Measurements on treatments wounds within individual rats were normalized to the gel only control wound as a baseline.

The ACT1-alone-treated wound had a scar that was smaller than the controls and most other treatments. However, the wound that received both the BMSC toroid and ACT1 had a scar that was even smaller in surface area than the ACT1-alone-treated wound. This finding of improved healing for the combinatorial treatment over all other treatments/controls was a consistent result. It was also noted that these same 2 wounds, Gel+ACT1 and Gel+BMSC Toroid+ACT1, showed consistent significantly faster closure rates than the other 4 wounds. Qualitative appraisal of the wounds indicated the following pattern of variance in scar size: Gel+BMSC toroid+ACT1<(smaller than) Gel+ACT1<Gel+BMSC Toroid<Gel alone=Gel+BMSCs (non-toroidal)+ACT1 wound=Gel+BMSC Toroid+Rev control wound. The same order of scar size variance in response to the treatment and control conditions was also observed. Importantly, the combinatorial treatment of gels containing the toroid of BMSCs and ACT1 consistently had the smallest scars at the end of the 30-day experiment.

The novel composition and method described herein represents a transformative technology in wound healing, greatly enhancing the performance of a number of other wound healing therapies. Current therapies based on stem cells usually involve the introduction of dispersed cells into a diseased organ with little regard for the synchronization and activation of the potentiality of these cells for regenerative repair. Here, the present example provides evidence that this widely used approach of randomly introducing stem cells may not be effective, perhaps even deleterious. Only when stem cells were primed in the culture dish using the present method prior to engraftment into a wound, was there seen a subsequent dramatic improvement in the regenerative healing of the treated animal. It is also that the activation of cells within the gel can be undertaken in the subject in situ, following a brief priming period in which the cells are attached to the gel in a culture dish. The present disclosure can be used coincident with the injury or can be introduced to a site on the subject prior to a surgery or any anticipated tissue-disrupting procedure (e.g., non-surgical dermabrasion) in order to precondition that site for the purpose of scar reduction, improved tissue structure and function and regenerative repair. Constituents of the present disclosure (e.g., EMT-primed cells, ACT1 and TGF-B3) can also be delivered alone or together for the purpose of preconditioning. The pre-conditioning can be at or repeated at 1, 2, 3, 4, 5, 6 hours or any other interval up to 24 hours. The pre-conditioning can be at or repeated at 1, 2, 3, 4, 5, 6 or any other interval up to 48, 72, and 96 hours and up to a week. Following preconditioning and surgery further post-treatment with the invention or constituents thereof can be undertaken. The data outlined in the present disclosure have the potential to revolutionize the standard care for cell-based therapies of injuries or any therapeutic approach in which stem cells are used as a therapy for patients.

To estimate the amount of granulation tissue, scar surface area and density of follicles in scar epidermis, a serial histological sectioning through each healed 30-day wound was performed. Following fixation for 4 hours in 4% paraformaldehyde, excised wounds and surrounding skin were processed for standard embedding in paraffin epidermal surface-up. The blocks were then serial sectioned at 10 um normal to the epidermal surface. From wound edge to wound edge every 30th section was mounted on a glass slide and stained with H&E histochemistry. Images of the granulation in each section were then recorded as single images or montages of 2-3 images. Generally 15-30 serial 300 um-spaced sections were recorded per wound. The granulation tissue area, length of epidermal surface and number of follicles intersecting the epidermis were then counted or measured using ImageJ from each wound montage. To obtain an estimate of wound granulation tissue volume the granulation tissue area measurements recorded for each section were entered into MS Excel and the number and spacing between sections were used in estimates of scar volume. Similarly, scar surface area was estimated from the linear measurements of epidermis from each section and number and spacing between sections. Follicle density in the scar epidermis was calculated by dividing follicle counts by scar surface area.

T-tests for paired samples were carried using MS Excel ($p<0.05$). Measurements on treatments wounds within individual rats were normalized to the gel only control wound as a baseline.

Figure 6:
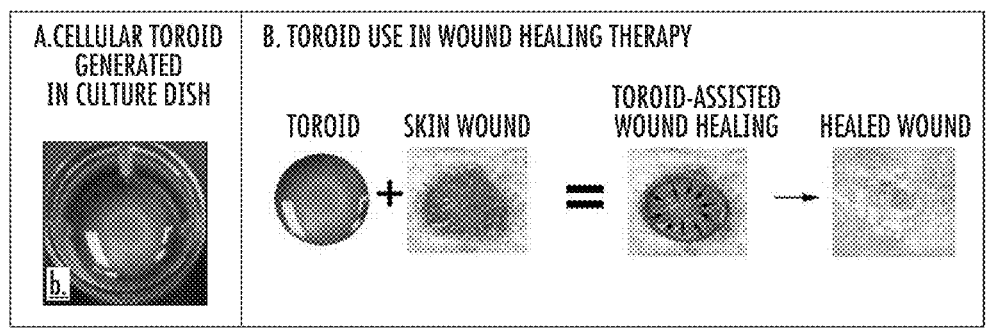
FIG. 6 illustrates toroid use in wound healing.

The following example further exhibits a treatment method using toroids dramatically reduces scar tissue formation following wound healing. FIG. 5a illustrate a toroid prepared in a collagen gel as outlined in the earlier example. An experiment was undertaken using novel compositions in a wound healing application (i.e., FIGS. 5a and 6b).

In these experiments, a circular collagen gel containing a toroid was generated comprised of rat bone marrow-derived stem cells. The gel and the BMSC toroid was then sutured into a circular 1 cm diameter excisional wound on an adult rat (FIG. 8b). The treated wound was done in association with 5 other control/treatment wounds on the same rat—i.e., there were a total of 6 equally sized 1 cm diameter wounds on the rat—see FIG. 8a.

Figure 7:
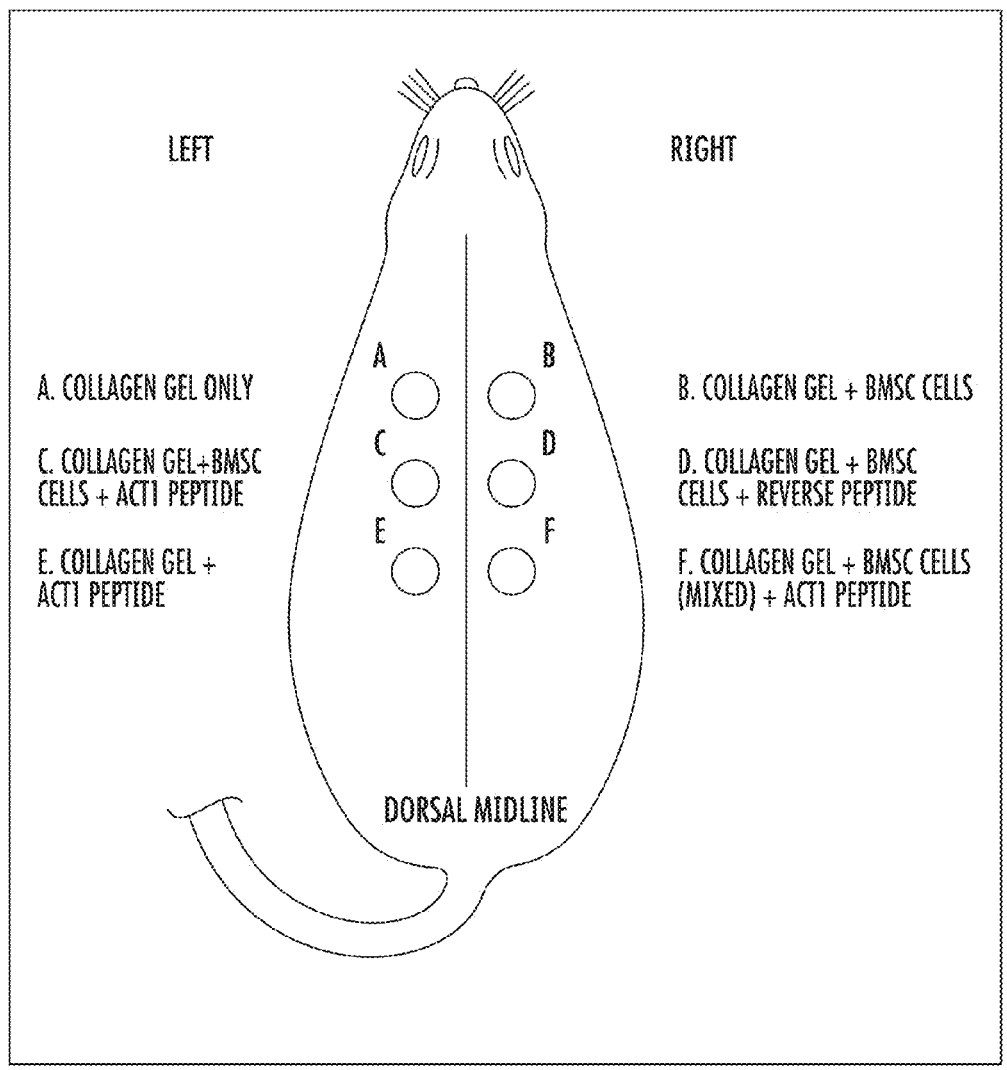
FIG. 7 illustrates the layout of the equally sized treatment/control wounds on either side of the dorsal midline of a rat.

From caudal (head) to tail and left hand to right hand the 6 wounds were treated as follows (See FIG. 7):

1. The top (i.e., caudal) left hand wound on the rat dorsal mid-line received a circular collagen gel containing no cells or other treatment (Gel-only CONTROL). This wound was considered a non-treatment control and was expected to heal in a manner comparable to any wound of 1 cm diameter on a healthy rat.

2. The top right hand wound received the collagen gel containing the toroid of BMSCs, but no other treatment (Gel+BMSC Toroid treatment wound). This treatment tested the effect of a toroid comprised of BMSCs on wound healing.

3. The middle left hand wound received the collagen gel containing a toroid of BMSCs+ACT1 at 150 uM (Gel+BMSC Toroid+ACT1 treatment wound). This tested the effect of a combinatorial treatment of a toroid comprised of BMSCs and ACT1 on wound healing.

4. The middle right hand wound received the collagen gel containing an induced toroidal ring of BMSCs+reverse control peptide at 150 uM (Gel+BMSC Toroid+Rev control wound). This treatment controlled for the effect of the Cx43-based peptide (i.e., ACT1) in a combinatorial treatment.

5. The bottom (i.e., tail) left hand wound received the collagen gel containing ACT1 alone (i.e., no cells) at 150 uM (Gel+ACT1 treatment wound). This treatment was a positive control, as it is already established that ACT1 speeds wound healing and reduces scar tissue—in mouse and pig models.

6. The bottom right hand wound received the collagen gel containing BMSCs pre-mixed into the gel, but not activated into a toroidal ring+ACT1 at 150 uM (Gel+BMSCs (non-toroidal)+ACT1 wound). This important control examined whether it was necessary for the stem cells to be subject to the novel steps for inducing toroidal morphogenesis in vitro, before being applied in combination with ACT1 to wounds.

The experiment was repeated on an additional 4 rats i.e., there were a total of n=5 rats each receiving 6 wounds. The 5 rats were allowed to heal for 30 days, during which time photographs were taken of the healing skin on each rat at set intervals. At the end of the 30 days, the wounded skin of each rat was sampled for histological analyses of scar tissue.

Figure 8:
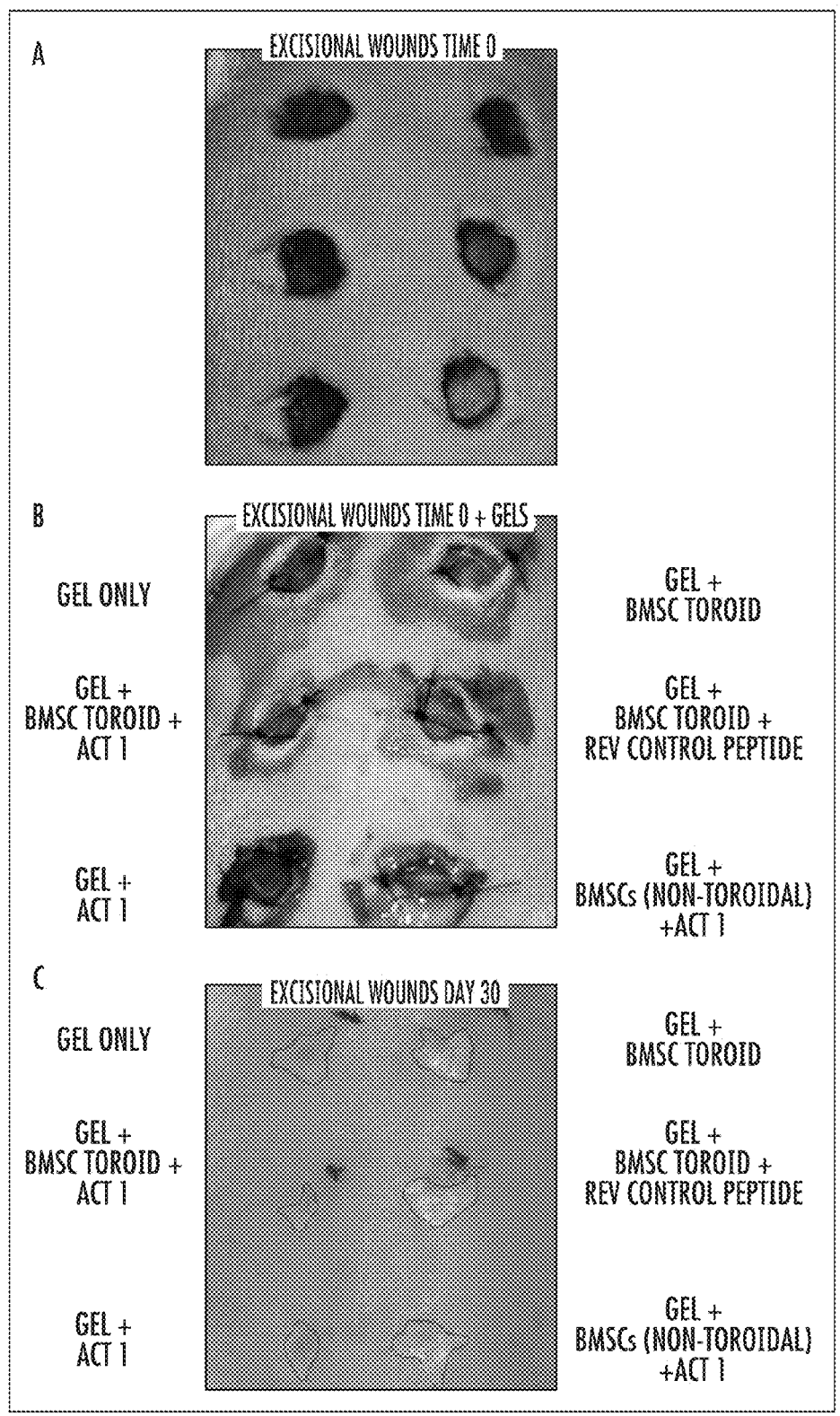
FIG. 8 illustrates that combinatorial treatment including a bone-marrow derived stem cells (BMSC) toroid promotes dramatic reduction in skin scarring.
Figure 9:
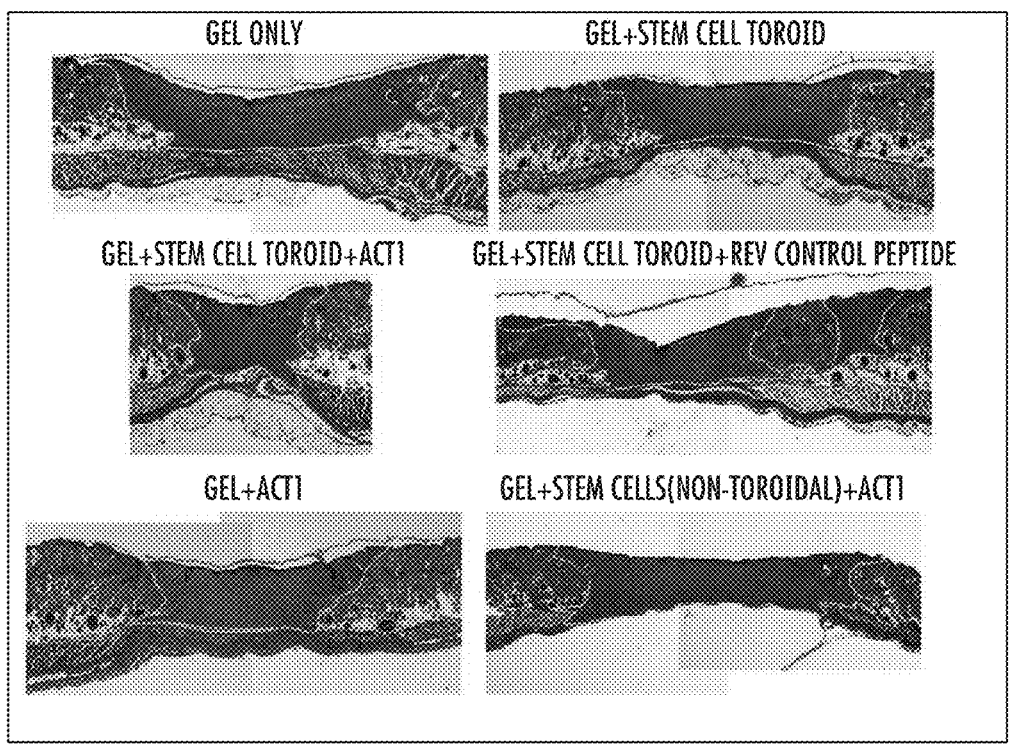
FIG. 9 illustrates a histological demonstration that the combinatorial treatment including the BMSC toroid (but not when BMSCs are mixed in the gel) dramatically reduces scar tissue formation and promotes epidermal/dermal regeneration.

FIGS. 8 and 9 are all from the same rat and are representative of results from the other rats.

In FIG. 8a, the six equally sized 1 cm diameter wounds cut on the dorsal mid-line of a rat are shown prior to treatment on day 1 at the beginning of the experiment (i.e., time 0). In FIG. 8b, these same wounds are seen with each of the 6 gel treatments sewn in and secured by 2 small sutures. FIG. 8c shows the healed scars from each wound at the end of the 30 day experiment. The scar boundaries are outlined in red. Note from FIG. 8c that the "Gel-only" control and the control wounds on the right hand side of the rat had scars of similarly large dimensions. As expected the ACT1-alone-treated wound had a scar that was smaller than the controls and most other treatments. However, the middle left hand wound that received both the BMSC toroid and ACT 1 had a scar that was even smaller in surface area than the ACT1-alone-treated wound. This finding of improved healing for the combinatorial treatment over all other treatments/controls was a consistent result in the 5 rats studied.

It is also noted that these same 2 wounds, Gel+ACT1 and Gel+BMSC Toroid+ACT1, showed significantly faster closure rates than the other 4 wounds. This result again was consistent between the 5 rats.

Serial histological sectioning was undertaken through the volume of each healed 30-day wound (i.e., on 20+ scars/wounds), three-dimensional volumes of wound granulation tissue were reconstructed (i.e., the scar progenitor tissue) and the volume the volume and surface area of the granulation tissue were carefully measured, as well as regeneration of hair follicles in the epidermis overlying the healed wound.

FIG. 9 shows H&E histochemical stainings of single sections from the middle of each of the six healed wounds from the same rat as shown in FIG. 8. These sections were one of the 10-20 serial sections taken per wound used for three-dimensional reconstruction of scar volume. Qualitative appraisal of FIG. 8c indicates the following pattern of variance in scar size: Gel+BMSC Toroid+ACT1<(smaller than) Gel+ACT1<Gel+BMSC Toroid<Gel alone=Gel+BMSCs (non-toroidal)+ACT1 wound=Gel+BMSC Toroid+Rev control wound. FIG. 9 confirms the same order of scar size variance in response to the treatment and control conditions. Importantly, the combinatorial treatment of gels containing the toroid of BMSCs and ACT 1 consistently had the smallest scars of the 6 wound conditions tested at the end of the 30-day experiment.

Figure 10:
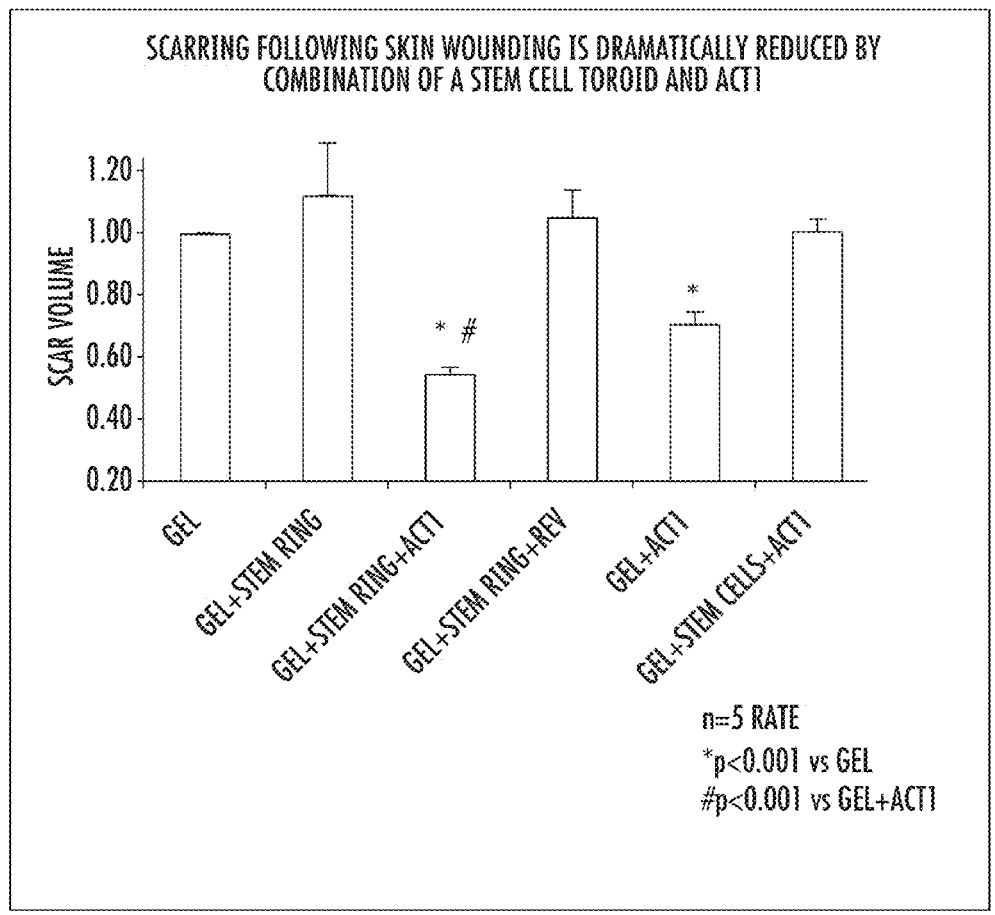
FIG. 10 illustrates a quantitative analysis that shows that a treatment of a BMSC toroid and ACT1 (but not when BMSCs are mixed in the gel with ACT1) provides statistically significant reduction in scar tissue formation following skin wounding.

Referring to FIG. 10, a statistical analysis of the data from quantitative wound histology was consistent with the qualitative appraisal.

Gel+ACT1 and Gel+Stem Toroid+ACT1 had significantly smaller volumes of granulation tissue than the other 4 wound control/treament conditions ($p<0.001$). Moreover, the Gel+Stem Toroid+ACT1 treatment scars were significantly smaller in size/volume than wounds receiving Gel+ACT1 alone ($p<0.01$). Quantification of scar surface area showed similar results. Note also the increased density of hair follicles in the toroid+ACT1 compared to the other control wounds. For example, compared to the Gel-only control, the combinatorial toroid+ACT 1 treatment provided a highly significant (p<0.00001) 275% increase in follicle density in the wound epidermis. This result demonstrates that the scar reduction prompted by the combinatorial treatment was accompanied by a striking regeneration of normal skin histoarchitecture.

An interesting feature of the quantitative analysis was that the combinatorial treatment of Gel+Stem Cells (non-toroidal)+ACT1 wounds did no better than the Gel alone control. Indeed, in some rats it appeared that this combination did worst of all compared to the other conditions applied to wounds. This result indicates that in the context of the experiment, BMSCs must be morphogenetically transformed into the embryonal-like composition for the combinatorial effect to occur. Moreover, the results indicate that stem cells that are not composed in the provided composition, even the presence of ACT1, are not sufficient to provide benefit during wound healing. These results indicate that the combinatorial effect of the provided composition with ACT1 will benefit to wound healing and scar reduction over and above each of these two factors alone.

The toroid effects are likely contributed to by signaling factors from its constituent cells, in addition to biomechanical forces, genetic and epigenetic influences exacted by the provided composition. As such, conditioned media or factors secreted by BMSCs when organized in the composition contribute to the combinatorial effect. As outlined elsewhere in the present disclosure, this combinatorial effect will be observed in conditions that include delivery with the provided compositions, cell-free extracts from the compositions, extract components and/or conditioned media from the provided compositions.

The results outlined herein indicate that the presence of cells alone in the wound were not sufficient to promote regenerative healing. The cells need to be prompted to undergo the morphogenetic transformation induced by the steps described herein for optimal scar reduction/regenerative healing effects.

Figure 11:
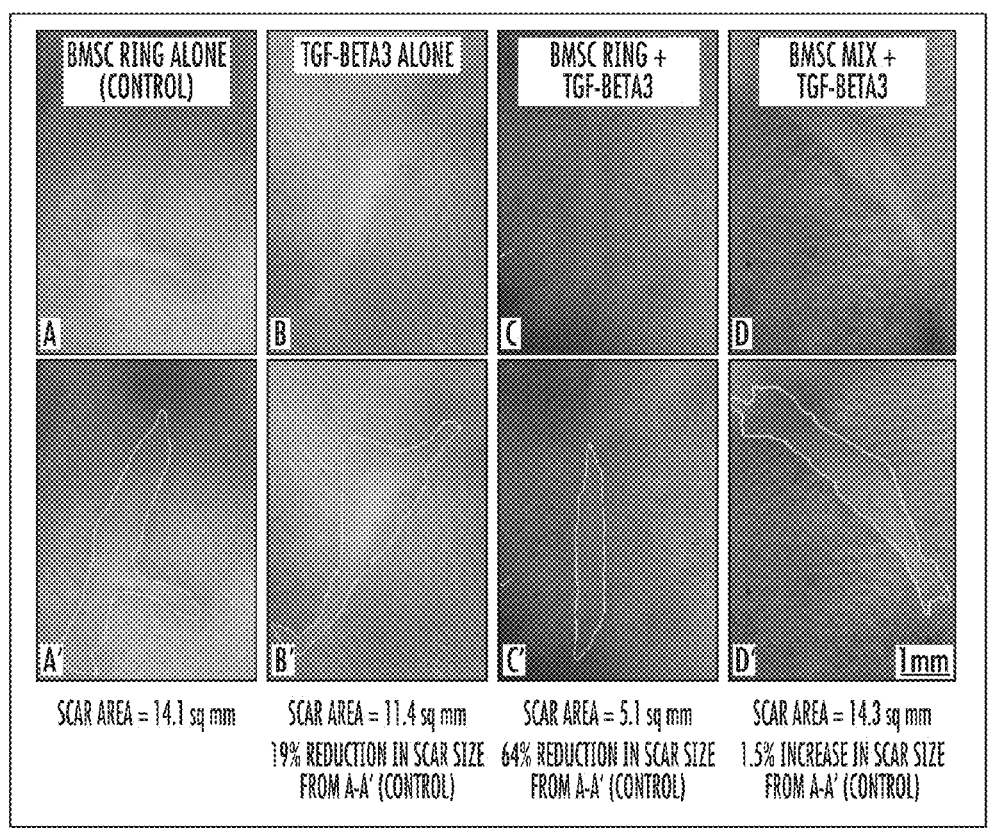
FIG. 11 illustrates a quantitative analysis showing that a combinatorial treatment of a BMSC toroid and TGFb3 (but not when BMSCs are mixed in the gel with TGFb3) provides significant reduction in scar tissue formation following skin wounding.

In still another example, FIG. 11 illustrates three healed 31 day-old scars from full-thickness 1 cm circular excisional wounds performed on the dorsal mid line of the same adult rat. All 3 wounds were generated on the rat on day 1 of the 31 day healing time course within the same 30 minute period of surgery. Healed scars were exposed by shaving the rat and depilating with Nair™ on day 31. Scar is delineated by a relative lack of hair follicles and variable skin tone-generally lighter and/or more heterogeneous than surrounding skin.

FIG. 11 A-C show the scars without annotation. A'-C' show the same scar areas on each healed wound outlined in black.

A) Wound immediately received the toroidal ring of bone marrow stem cells (BMSCs) in gel (BMSC+Gel) following the surgery on day 1 of the experiment. As shown elsewhere in 4 other rats, this treatment condition resulted in a scar at ~30 days whose superficial appearance did not differ significantly from control wounds receiving only collagen gel. The scar in A thus serves as a comparative control for the other two scars shown in the FIG. 11 (i.e., B and C).

B) Injury received 3 ng/ml TGF-B3 in a collagen gel immediately (TGF-Beta3+Gel) following surgery on day 1 of the experiment. TGF-B3 treatment caused a 19% reduction in the superficial area of visible scar.

Figure 12:
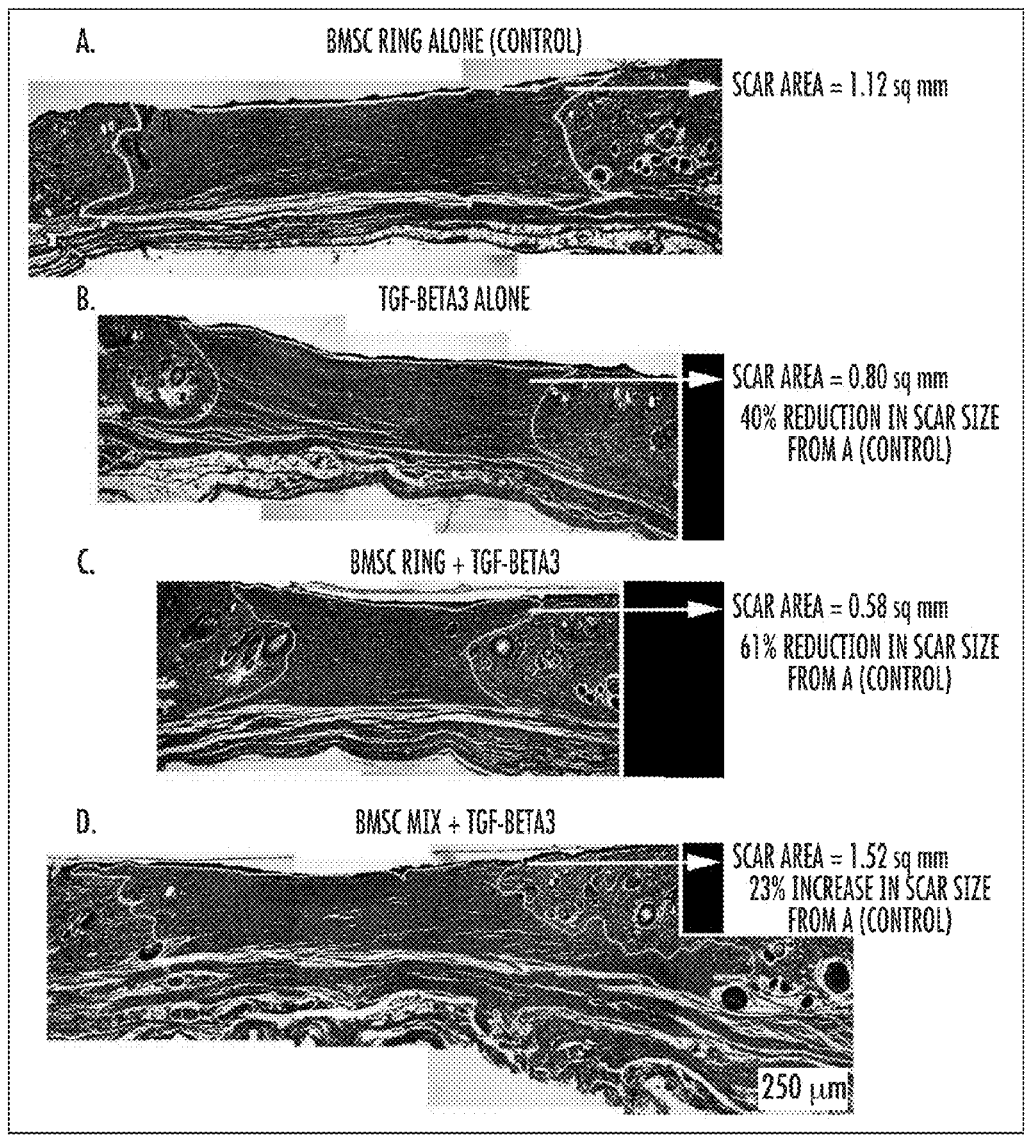
FIG. 12 illustrates a histological demonstration that the combinatorial treatment including the BMSC toroid with TGFb3 (but not when BMSCs are mixed in the gel with TGFb3) dramatically reduces scar tissue formation and promotes epidermal/dermal regeneration.

C) Injury received the a toroidal ring of activated BMSCs together with 3 ng/ml TGF-B3 in the collagen gel (BMSC+ TGF-Beta3+Gel) immediately following surgery on day 1 of the experiment. Similar to data in this disclosure showing that a combinatorial treatment of a toroid of BMSCs with ACT1 causes striking reduction in scar area, it was determined that a combinatorial treatment of a BMSC toroid and 3 ng/ml TGF-B3 results in a 64% reduction in scar size compared to the wound receiving the BMSC toroid control (A-A') and a 55% decrease in scar size compared to the wound treated with TGF-B3 alone. Note that the tone and uniformity tone of the scar in C matches the surrounding skin more closely than that seen in the scars in A and B. These trends are confirmed in the histological analyses in FIG. 12.

Based on these data it is concluded that activated BMSCs in the gel constructs described herein combine with compounds including ACT1 and TGF-B3 to promote scar-free healing in an embryonal-like manner. Thus, either ACT1 or TGF-B3 when provided acutely alone reduces apparent scar area. However, when either is given in combination with a BMSC toroid, both ACT1 and TGF-B3 prompt even greater reductions in scar size compared to controls and to when ACT1 and TGF-B3 are used alone. ACT1 and TGF-B3 are contemplated to be 2 members of a broad class of factors as described further herein that combine with cells activated as provided in the present disclosure to promote scarless, embryonal-like healing in an adult tissue. As was the case with the combinatorial treatment of ACT1 and cells mixed into the gel, when TGFb3 was given with BMSCs mixed into the gel the benefits on scar reduction and improved regenerative healing seen with the TGF-B3 and the present disclosure were not observed.

Examples from Heart

A therapy capable of regenerating cardiac muscle lost by injury or disease has not yet been convincingly demonstrated. Excess formation of scar tissue is the normal response to injury or disease in the human heart, not regeneration. Tipping the balance from the normal scarring response to regeneration in the heart has thus far proved difficult, if not impossible. The provided compositions will be provide a means of regenerative repair of the heart following disease (e.g., heart attack), surgery, injury of congenital malformation.

One of the commonest injuries to the heart is a myocardial infarction (MI) that occurs as a sequalae to coronary heart disease (CHD). CHD is the biggest killer of people in developed countries. During an MI or "heart attack" there is a sudden failure of coronary circulation. If the patient survives, the MI scar may cause sickness or death from loss of cardiac function (heart failure) or prompt the development of life-threatening arrhythmias. The "EMT-primed" cells in the provided invention would be deployed to reduce scarring following MI and thus ameliorating morbidity and mortality associated with CHD.

Figure 13:
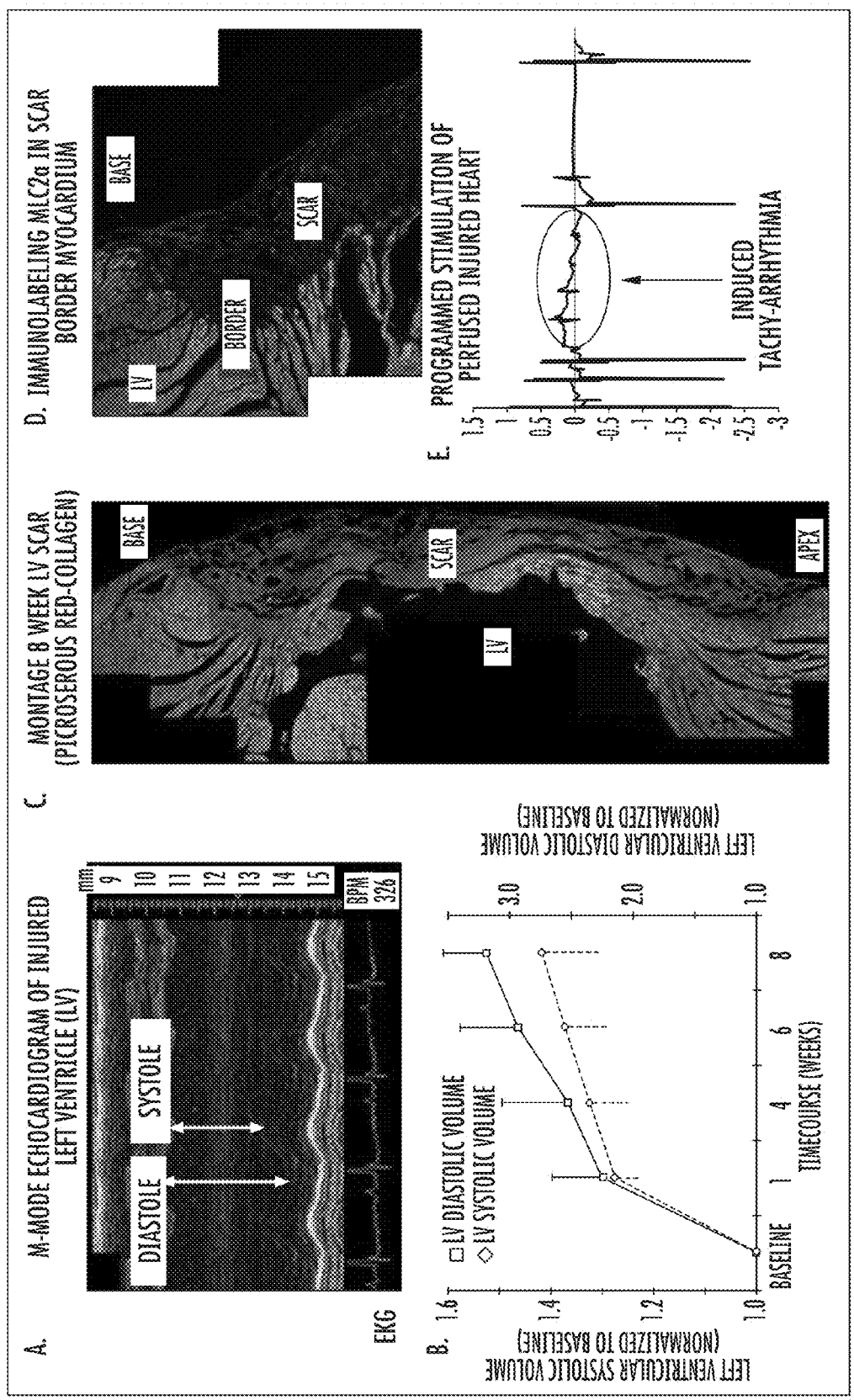
FIG. 13 illustrates the heart injury model in rat developed to test regenerative repair of heart by the disclosed invention.

A new method has been developed for injuring the heart in an animal model that was specifically designed to increase the ability to determine whether the therapeutic approach causes regeneration rather than the normal process of formation of scar tissue following an injury such as MI (FIG. 13 and O'Quinn et al. *Circulation*, 118: 495, 2009, incorporated by reference herein). This method involved delivering a freezing injury to the heart that always generated a non-transmural wound of consistent size and depth in the left ventricular wall muscle. Because wound size was consistent between mice, the exact amount of scar tissue that would be deposited in the heart in each animal injured can be ascertained. More importantly, the consistency of the lesion enabled the determination with certainty that has not been previously achievable by others as whether newly regenerated muscle was present in the healed injury. Example of the usefulness of this injury method in detecting control and treatment effects on regeneration of myocardial structure and function is provided below.

To undertake the novel injury model, 12-24 wk female CD1 mice (Charles River) were used. Mice were anesthetized (isoflurane), intubated and a left thoracotomy was performed at the 4th intercostal space. The LV wall was cryo-injured by exposure for 5-sec to a liquid-$N_2$ chilled 3 mm circular flat-tip probe (Brymill: CRY-AC-3) such that the LV surface was slightly depressed. In the case of treatment of the animal model with the composition cryo-injury, the mouse receives EMT-primed BMSCs in gel together with 3 ng/ml of TGF-beta3 over the cryo-injury, and the gel is then held by 2 small dissolving sutures on the surface of the epicardium. Cel-Tak™ adhesive (BD Biosciences(11)) or other surgical adhesive can also be used to secure the gel to the wound. Surgical wounds are then closed using 6-0 silk sutures (Ethicon) and sealed with Nexabond™.

In another example of an MI injury adult (12-24 wk) CD1 mice are used. Mice are anesthetized and a left thoracotomy performed at the 4th intercostal space to expose the heart. A suture is then placed through ventricles mid-way down the anterior interventricular branch of left coronary artery and great cardiac vein. The suture is tied, blocking off perfusion of the ventricle below the level of the occluded artery causing an MI-like mouse model of a human "heart attack". Cel-Tak™ adhesive (BD Biosciences(11)) is then used to secure treatment gels containing EMT-primed BMSCs together with 150 uM ACT over the cryo-injury.

The gels containing toroidal rings of EMT-primed mouse BMSCs are generated as follows. Bone marrow is collected from the femurs and tibiae of adult (12 week old) CD1 mice, pooled and CD45+ mononuclear cells isolated by gradient separation and FACS-sorting. Following isolation, dispersed BSMCs are added to the top of pre-polymerized collagen gels in 6-well microplates and the cells allowed to attach over 24 hours in a fortified media that supports BSMC survival. The gel/cells are then detached from well walls and the free floating gels cultured for a further 24 hours, over which time the characteristic toroids form in the gel.

Mouse iPS cells are generated from murine skin fibroblasts by transduction with OCT4, SOX2, c-MYC, and KLF4 carried in a retrovirus as described previously (Li et al. *J Cell Biochem.* 2009; Takahashi and Yamanaka. *Cell.* 2006; 126(4): 663-676, incorporated by reference herein). The iPS cells generated from mouse skin fibroblasts will be maintained on irradiated MEFs feeder layers in standard ES medium. Validation of reprogrammed state of murine iPS cells will be done using antibodies to nuclear marker Nanog, and the surface markers, TRA-1-60 and Ssea4. Following transduction with the reprogramming retrovirus reprogrammed cells will be tested for stemness as evidenced by their having achieved significant milestones including 1) proviral silencing (i.e., silencing of viral vector encoded GFP) and 2) induction of endogenous Nanog expression. With further culture these GFPdim/−, Nanog+ cells go on to express TRA-1-60 as described by (Chan et al. *Nat. Biotechnol.* 2009; 27(11):1033-1037, incorporated by reference herein). One iPS cells are confirmed the cells will be EMT-primed in gels as described in the preceding paragraph for BMSCs.

Following surgery and application of the gel and EMT-primed BMSCs (or EMT-primed iPS cells) to either freezing or ligation injuries of the heart, mice are ventilated until respiring spontaneously, warmed and given analgesia until recovery. Following surgery the mice are measured weekly for heart function using M-mode echocardiography for a 6-12 week period. Some hearts are also tested for propensity to develop arrhythmias using an induced arrhythmia protocol and electrical activation mapping with voltage sensitive dye as has been described previously (O'Quinn et al. *Circulation,* 118: 495, 2009, incorporated by reference herein) At the end of the said period the mice are sacrificed and the healed cryo-injured hearts are assessed using standard histological and immunohistological approaches for scar tissue formation and regeneration of new cardiac muscle in place of what would normally be scar in a untreated control animal.

Using the said cryo-injury model in a mouse model, it has been shown with confidence (i.e., $p<0.05$), for example, that release of ACT1 from a methyl-cellulose patch directly on the injury results in significant improvement in LV diastolic and systolic function over a 8 week time course (n=21 animals). This improvement in mechanical function was associated with significantly increased scar uniformity. Treated hearts also showed higher and more uniform Cx43 in myocytes bordering the scar, as well as elevated levels of phosphorylated s368 (ps368) Cx43 from as early as 2 hours following injury. ps368 upregulation is associated with ischemic pre-conditioning and this elevation of ps368 contributes to the beneficial effects of ACT1 following myocardial injury. It is also expected that delivery of ACT1 or other agent (e.g., TGF-B3) in a pre-conditioning period prior to injury will have a beneficial effect and that this effect will be improved still further by the further delivery of the provided invention. Consistent with evidence that downregulated and disordered Cx43 at the infarct border zone is a key factor in cardiac conduction disturbance, it has been determined that there was a dramatically reduced ($p<0.05$) frequency and severity of arrhythmias in ACT1-treated animals as assessed by electrophysiological studies (pacing and S1-S2 protocols) (n=22 animals) (O'Quinn et al. *Circulation,* 118: 495, 2009).

In another example of the novel method, analysis of heart pump function by echocardiography showed that one week following injury in a second group of treatment mice (mice in which bone marrow containing stem cells was infected with an shRNA lentivirus) and control mice (i.e., mice similarly receiving a control virus) showed a similar (~20%) decline in the efficiency of heart pumping function—as measured by % ejection fraction from the left ventricle. Ejection fraction is a standard clinical measure of cardiac pumping efficiency. This decline indicated that just after freeze wounding both treatment and control hearts had received a similar initial degree of injury as reflected by their similar reduction in function over the first week. However, at the end of the following 4 weeks, a stage at which it would be expected that the healing of the injury to the heart and scar formation to be nearing completion, cardiac pump function of the treatment had improved to be <98% better than that of controls. Remarkably, by 4 weeks heart pump function in the treatment had recovered to levels identical to those of a normal uninjured heart. Meanwhile in controls, pump function had declined at the 4 week period by 50% compared to uninjured hearts.

The improvement in % fractional shortening of the left ventricle is another clinically used measurement of cardiac function and contractility. Percent fractional shortening improved by more than 120% in the treatment relative to control at 4 weeks following injury. As was the case with ejection fraction, treatment caused a recovery of % fractional shortening levels to those of a normal, uninjured heart at 4 weeks, whereas controls continued to show significant declines in this index of cardiac contractile function.

The systolic and diastolic volume of the left ventricle during the cardiac contraction cycle are two other commonly used indices of cardiac function. Increases in these indices are recognized as indicative of a loss of cardiac function and are viewed by clinicians as disease markers for the development of eventual heart dilation, heart failure and death. The diastolic volume of the left ventricle of treatment was significantly improved, being 40% less dilated than that of control. More remarkably, left ventricular systolic dimension was improved to be >75% lower than controls. Putting this another way, at 46.5, the left ventricular volume of control at systole was 5-times more dilated at systole than that of the 10.61 value measured from the echocardiograms of treatment. Treatment also caused both left ventricular volume indices to recover to levels found in the normal, uninjured heart. No such recovery to normality has ever been noted to occur in controls.

The data at 4 weeks post-injury led to the conclusion that the mice that had received standardized cardiac injury and treatment unexpectedly recovered to normal cardiac pump function and contractility. In further contrast to controls, there was no sign of pathological cardiac dilation indicating that treated hearts were progressing to heart failure and eventual death.

Echocardiographic measurements of % ejection fraction, % fractional shortening, and left ventricular volume at diastole and systole were repeated at 6 weeks. These measurements indicated that the improvement in these parameters found at 4 weeks were sustained 6 weeks following treatment and injury. By contrast, none of these cardiac function parameters showed any improvement in the control at 6 weeks and were for most part were similar to the depressed measurements taken in controls at 4 weeks. Indeed, left ventricular volume at diastole showed further significant deterioration in the control indicating a continuing progression toward heart failure in the untreated control.

Second, the unexpectedly large beneficial effects on regeneration of cardiac muscle and reduction of scar in the injured heart were noted. Following echocardiography at 6 weeks, hearts were removed for morphological and histological analyses. A large pale scar was evident on control hearts with no sign of regeneration. This large scar extended nearly to fully incorporate the boundaries of the initial injury. By contrast, the area of initial injury in a treated heart showed only a minimal amount of visible scar at the 6 week time point. In quantitative terms, less than 10% of the initially injured area on the control heart is cardiac muscle. By contrast, the treated heart showed a 70-90% regeneration of normal cardiac muscle. Thus, in summary the unexpected ability to prompt a full recovery of function in treated hearts is correlated with an equally impressive and unexpectedly extensive regeneration of normal cardiac muscle at the injury.

That regenerated muscle was present was further confirmed by histology of the hearts. Myocytes in treated hearts were found throughout the scar with a particular concentration of these cells near the epicardial border of the scar. This sub-epicardial population was notable for a number of reasons. First, it is direct evidence for myocardial regeneration. The freeze injury is via a liquid nitrogen-cooled probe applied to the outer surface of the heart generating a hemi-spherical injury volume. During the freeze injury, the broadest sector of lethally frozen tissue is at the epicardium just under the freezing probe, i.e., the site where the "new myocytes" can be seen after 4 weeks of healing. Thus, this zone of sub-epicardial "new myocytes" must have regenerated over old necrotic tissue frozen near the epicardium—the previous cells at this location could not have survived the freeze injury. Indeed, in more than 20 control hearts subject to standardized freeze injury evidence of regeneration at the sub-epicardium was never seen. Second, the myocytes in this sub-epicardial zone were compact and highly aligned. This means that the treatment methods of the present disclosure had not only induced "new myocytes", it had also the regenerated the precise tissue organization that existed at this locale in the heart prior to injury. Thus the treatment had unexpectedly regenerated structure at both cellular and tissue scales—i.e., in addition to restoring function at the organ level. Thirdly, it is noted that these "new myocytes" are contiguous with adjacent myocardium. Cx43 immunolabeling indicates that these new myocytes also express the gap junction protein. Such tissue organization is consistent with electromechanical integration with surrounding myocardial tissues and the lowering the likelihood of arrhythmia. As noted previously, it is contemplated that the novel composition of the present disclosure will prevent arrhythmias.

It can also be noted that the collagen staining appears significantly paler in the treated hearts indicating that collagen organization is different from that of controls. Whereas much cardiac research is focused on attempting to promote adult myocyte cell cycle re-entry to regenerate cardiac muscle, the novel approach described herein leads to modification of scar organization in vivo. It is posited that the scar in the treated animals is a "better scar," permitting a new type of remodeling of this region with new myocytes. Finally, the section reveals that the extent of scar tissue as indicated by comparing the area of scar tissue is significantly less (>60-70% less) in the treatment compared to controls. This means that the treatments of the present disclosure can have an unexpectedly profound effect of tipping the balance between scar formation, organization and inducing a multiscalar regeneration of functional myocardium in the injured heart.

In a further example in heart, the provided composition can be introduced via keyhole surgery in a human subject who has suffered an MI (i.e., preferably within 1 week of the MI) under full anesthetic by a surgeon into the minimally disrupted pericardial sac of the subject via a catheter. The stem cells activated (i.e., EMT-primed) by the method described herein in the composition are derived from a tissue-matched non-autologous source or taken from the subject themselves. For example, from previously sampled and stored bone marrow stem cells biopsied from the patients hip or peripheral blood or iPS cells generated from the subjects own skin fibroblasts according to standard protocol. The surgical wound in the patient's skin is repaired by a small suture and the patient allowed to recover.

In another example, the compositions would be sutured or secured by sterile surgical adhesive into place over an acutely healing MI while the subjects heart is exposed during coronary artery bypass graft surgery (CABG) and the like. Following CABG surgery the healing of the myocardium of the subject would be monitored for improvement in cardiac function by routine EKG, ambulatory EKG, echocardiography, blood assays and other tests of cardiac well being and healing that a qualified clinician deemed necessary for the recovery of the subject.

Examples from Spinal Cord

Subjects with acute spinal cord injuries to the central nervous system (CNS) represent a seriously problematic group for whom even a small neurological recovery of function can have a major influence on their subsequent independence. The provided compositions would be especially useful in patients with a complete cord injury who normally have a very low chance of recovery. For optimal recovery of function the composition would optimally be applied acutely or sub-acutely within 1 week of the initial injury. The prognosis of incomplete cord syndromes would also be improved by the composition.

In one example, a subject with an acute anterior cord injury due to a flexion injury of the cervical spine would have surgery performed to expose the dorsal aspect of spinal cord at the level of the injury. A gel containing a toroidal ring composed of EMT-primed stem cells as described herein is then placed directly on the injury. Single or multiple compositions are applied depending on severity of the injury. The surgical wound exposing the spinal cord injury is then sutured shut, enclosing the composition in situ. The stem cells activated by the present method are derived from a tissue-matched non-autologous source or taken from the subject themselves (for example, from previously sampled and stored bone marrow stem cells or iPS cells generated from the subjects own fibroblasts). Improvement in function is assessed by a doctor at intervals (e.g., 6, 12, 26 and 52 weeks) following treatment by neurological outcome tests including assessments designed to measure motor activity, pinprick skin sensitivity and recovery of sensation. CT/MRI of the spine at the level of injury is also undertaken to monitor the healing progression of the subject. Medium- and long-term management would then be directed towards rehabilitation, including physiotherapy and occupational therapy to enable as full recovery of function as is possible following the treatment.

In one aspect the recovery of spinal function will occur because of regeneration of new spinal cord neural connections from stem cells. This reparative aspect will occur in other CNS and PNS (peripheral nervous system) tissues. In another aspect, the recovery of spinal cord function will be contributed to by reduction in inflammation, swelling, odema and tissue loss associated with placement of the composition. Assay of this can be tested in animal models. For example, following injury to rat spinal cord in vivo, rats are treated with the composition. Soluble fluorescein-isothionate-tagged BSA (bovine serum albumin) or Evans blue dye is then injected into the tail vein. Control animals show leakage of the dye from the vascular system into tissues within and surrounding the spinal cord. However, animals treated with the composition demonstrate only limited dye leakage, with it majorly being confined with intact vascular structures. In the case of the CNS tissues such as the brain and spinal cord, this is due to the composition promoting the maintenance of the blood-brain barrier. However, the maintenance of barrier function should in some aspect be seen in all tissues of the body. The results will thus indicate that leakage of the capillary-vascular system is not restricted to the CNS (e.g., spinal cord, brain, retina) and that a broader range of medical applications, such as for treatment of conditions of blood vessels, would benefit from treatment with the provided composition.

Spinal cord experiments are carried out on adult SD rats as previously described by Banik and co-workers (Sribnick et al. J Neurosci Res. 2006 October; 84(5):1064-75, incorporated by reference herein). Rats are anesthetized and laminectomies are performed at T-12. Trauma is administered by dropping a weight of 5 g from a height of 8 cm onto an impounder (0.3 cm in diameter; 40 g·cm force) gently placed on the spinal cord. Treatment gels (i.e., 5 mm diameter including EMT-primed stem cells) and controls (as per eye and heart injury) are immediately applied and wounds sutured closed. Spinal cord edema is assessed at 48 hrs post-injury, as described above. Cell death caused by compression injury is also assessed acutely on 5 µm sections of spinal cord from the lesion, which are co-labeled with NeuN and TUNEL staining as a marker for neurons and cell death respectively. Assessment of inflammatory cell infiltration (e.g., microglia and macrophages) will be done using OX42 and ED2 antibodies. To determine the long-term benefits of treatment of treatment with EMT-primed BMSCs; the functional and behavioral recovery of rats are tracked over time courses up 6 months following injury and NeuN and GFAP immunohistology will be used to assess glial scar and neurogenesis across the scar.

Examples from Eye

Normal eyesight is dependent on the transparency and regular curvature of the cornea. The histoarchitecture of the cornea is similar to that of skin—consisting of a stratified epithelium overlying a collagen-rich stromal matrix embedded with fibroblastic cells (e.g., keratocytes), although is largely avascular except at the periphery. Severe injury, surgery (Corneal refractive surgeries (CRS) such as photorefractive keratectomy (PRK)) and certain disease processes can lead to the loss of corneal transparency via activation of fibrotic/scarring processes in the corneal stroma. The resultant severe fibrosis of the cornea is difficult to treat and typically requires corneal transplant, which may lead to further complications. A safe and effective approach to reducing corneal scarring complication such as provided by the present composition would thus be welcomed by ophthalmologists and eye surgeons alike.

Minor scratches on the cornea are common and the composition is not envisaged to be used for normally healing minor injuries. However, the composition would be of use in the treatment of more serious injuries to the cornea that may occur from small flying particles when drilling, sawing, chiselling, grinding, lawn mowing, and so on without eye protection and also from chemical burns such as that resulting form caustic solutions, acids, wet concrete and the like. Also the composition would be used in patients receiving CRS/PRK surgeries that may present high risk profiles such as those displaying wide pupils or evidence of poor wound healing such as might occur in a diabetic patient.

Following standard sub-acute stabilization and cleansing by a clinician, a subject suffering a severe chemical burn would have a collagen gel containing a toroidal ring composed of stem cells and 180 uM ACT1 prepared as described herein, placed directly on the injury. Preferably the treatment would undertaken within 1 week of the initial injury. Single or multiple compositions can be applied depending on severity of the injury. Antibiotic eye drops would then be placed in the eye to prevent infection. The composition can also be place with a association membrane to further aid healing. The eyelid would then be temporarily sutured closed, to retain the composition and a bandage would then be placed over the closed eye. Painkillers such as paracetamol or ibuprofen would be used to ease pain over the subsequent healing process. 7-14 days later the lids would be released and repair of the cornea assessed by an ophthalmologist for inflammation, scarring and other clinical indications of corneal healing. The stem cells activated by the method described herein in the composition would be derived from a tissue-matched non-autologous source or taken from the subject themselves (for example, from previously sampled and stored bone marrow stem cells or iPS cells generated from the subjects own skin fibroblasts). Improvement in function are assessed by a doctor at intervals (e.g., 6, 12, 26 and 52 weeks) following treatment by vision tests. An eye patch to cover the eye would not normally be advised after 10-14 days following injury as this may impair the healing process.

Figure 14:
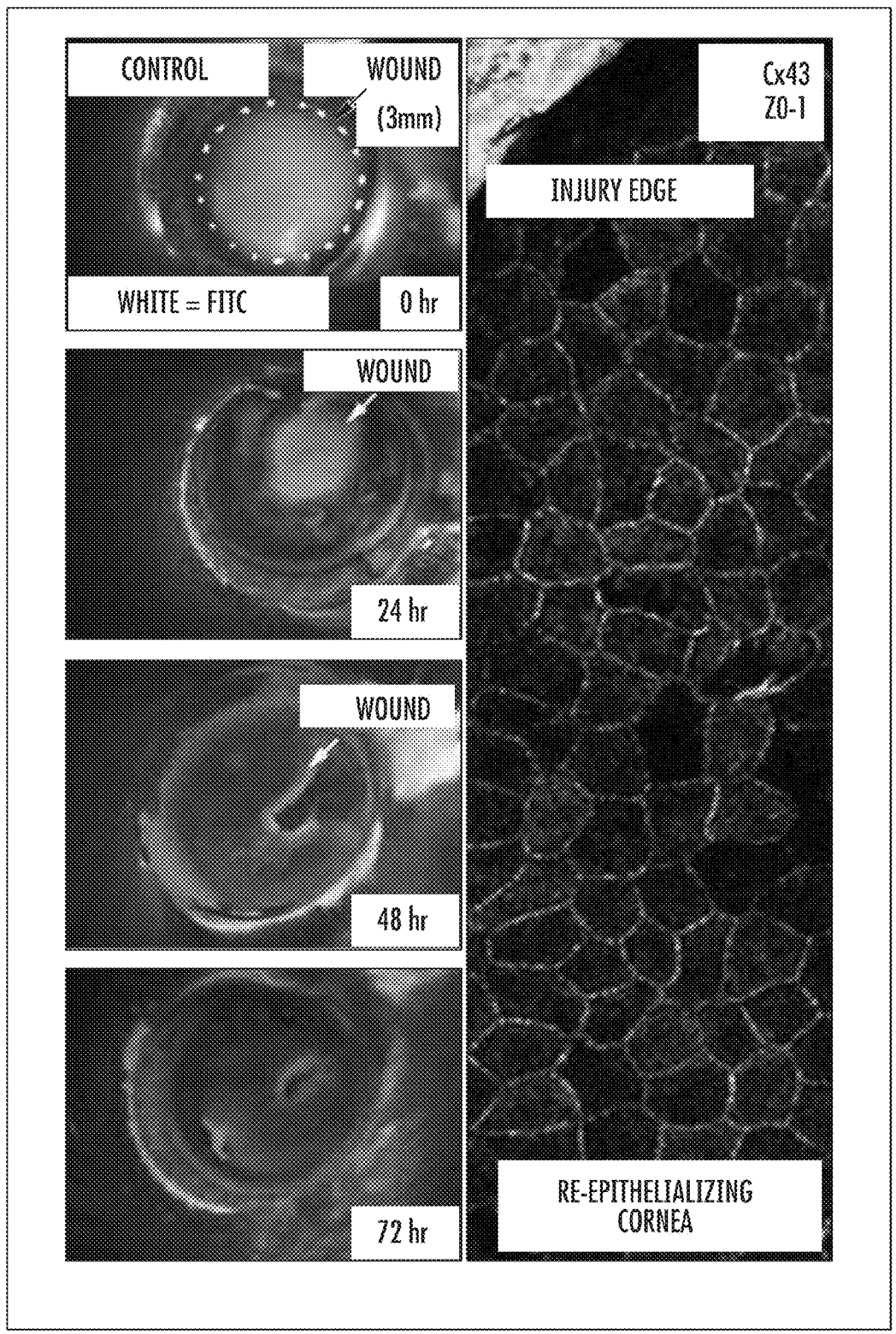
FIG. 14 illustrates the ocular corneal burn injury model developed to test regenerative repair of injured cornea by the disclosed invention.

An animal model of corneal injury has already been published (FIG. 14 and Chen et al. Invest. Ophthalmol. Vis. Sci. 2009; 50: 2480, incorporated by reference herein). In this model, adult (12 wk) SD rats are anesthetized and the central cornea treated with 20% ethanol for 30 seconds using a 3-mm marker placed on the corneal surface. The cornea is then thoroughly rinsed with saline and the loosened epithelial layer removed using a detaching spatula. A treatment (i.e., gel with EMT-primed non-autologous BMSCs) or control gel is then placed in the alcohol burn injury and the eye-lid sutured shut for 48 hours to hold the gel in place.

Corneal wound closure is determined by administering 0.25% fluorescein sodium eye drops and digitally capturing the cornea under a fluorescent stereomicroscope at 0, 48, 72, 96, and 120 (closure is usually complete by 120 hours in rat) hours post-injury (e.g., FIG. 14). Levels of scar tissue deposition and transparency is assessed on whole mounts of isolated corneas 30 days post injury. Corneal tissue are also be subject to standard histological and immunohistochemical studies on tissues sections to assess corneal epithelial and endothelial integrity and collagen organization and myofibroblast (alpha-SMA) density in the stroma.

Example from Tissue Engineering

Loss of skeletal muscle mass is an important problem for surgeons. Skeletal muscle has some ability to regenerate from endogenous stem cells called satellite cells. However, if the injury is large, this natural reparative ability can be overwhelmed. In such cases, muscle is not regenerated and scar tissue replaces lost muscle—if the patient is fortunate.

One clinically important example of injuries involving muscle that can be difficult to repair are ventral hernias (also known as incisional hernias). Annually, over 2 million abdominal operations are performed in the United States. (Millikan K W. Surg Clin N Am 2003; 83(5):1223). Given a failure rate for abdominal closures of 11 to 20 percent, it is not surprising that over 100,000 ventral hernia repairs are attempted each year in the United States alone. The incidence of ventral hernias has remained relatively stable over the last 75 years despite many medical advances.

The repair of ventral hernias typically involves the closing the hernia with a synthetic mesh or more recently decellularized human dermis (Alloderm, LifeCell). Although these methods effectively "patch the hole" they lack the ability to reconstitute the lost abdominal muscle. The mesh imparts no contractile function and with large hernias it is ineffective at producing counter pressure from the contracture of remaining abdominal musculature. These repair techniques do little to reestablish the dynamic role of the abdominal wall in support of the torso and lumbar spine. With adynamic repairs, force vector summation of abdominal wall contraction is focused on the repair itself Mesh repairs are also associated with bowel obstruction (5%), enterocutaneous fistulae (2-5%), and infection (1-2%). The aggregate incidence of long term complications associated with mesh repair approaches 27% (Mudge and Hughes L E. Br J Surg 1985; 72:70-1). The following example illustrates how the present disclosure can be used to repair an experimental ventral hernia in a rat—by extension in a human subject.

To create the ventral hernia model, 250 gram male Sprague Dawley rats are used. This size male rat has sufficient tissue for isolation of satellite cells, creation of the abdominal defect and has matured sufficiently to be considered adult in phenotype. After general anesthesia is achieved, the animal is prepped in standard surgical manner. A 1 cm×1 cm excisional wound is then generated in the abdominal muscle through to the cavity of the abdomen. To isolate autologous satellite cells from skeletal muscle of the same rat, a muscle biopsy (0.5 mm×0.5 mm×0.2 mm=05 cm$^3$) is extracted from the vastus lateralis and placed in mosconas on ice. This provides the 10 to 1 expansion of cells required to repair the defect, The biopsy wound is approximated and closed by suture. The sampled muscle tissue is rinsed vigorously with PBS at least three times to remove blood. The tissue is then minced thoroughly with scissors to dislodge adherent fat and washed several times with cold PBS. Warmed and gassed protease is added (sigma #P-5147; 1.25 mg/ml in Krebs Ringer Bicarb. Buffer (Cat #K4002)) to the tube with the tissue at a concentration of 1:5 (enzyme:tissue), followed by 1.25 hours shaking incubation at 37° C. The tube is centrifuged and the pellet is resuspended in 25-30 ml of high serum media (DMEM+25% Fetal Bovine Serum+1% Pen/Strep antibiotic+0.1% Gentamycin). DNAse is added and the tube is shaken vigorously and centrifuged to collect the sample. Spun supernatants are then panned onto 150 mm dishes with 25-30 ml media for 1.5 hours at 37° C. in the incubator. The cells are dislodged with 0.25% trypsin-EDTA when cells are at least 90% confluent, counted and seed onto CtCs. A sister culture of satellite cells is then created in collagen coated culture dishes. The cells are then characterized by immunolabeling for Pax 7, Myf5, MyoD, and sarcomeric myosin (MF20). In previous studies, the satellite cell cultures are 80+% positive for Pax7 and MyoD.

For generation of EMT-primed skeletal muscle stem cells, 30-50 collagen gels are prepared in 2 cm diameter circular wells as described above. Dispersed satellite cells (12×10$^6$ per well) are then applied to the well. The cells are allowed to attach and culture of the collagen substrate for 24 hours and then the gel is released as per standard practice for the present disclosure. Alternately, the gels can be released after cell attachment is achieved, static or dynamic strain is then applied to generate preferred alignment and differentiation potential of the adherent cells. The gels can also be soaked in ACT1, TGF-B3 or other compound assisting muscle regeneration by the stem cells.

Following a 24 hour period in culture, circular gels containing EMT-primed stem cells can then be stacked within a single well, each layer being adhered to the next by small dab of Cell-Tak™ at the gel edge. The cylindrical 3d assembly of gel layers with EMT-primed skeletal muscle cells then has a suture threaded through the middle of its long axis, removed from the culture well and then placed in the open excisional wound in the abdominal muscle of the rat. The suture thread through the cylinder of EMT-primed stem cells stabilizes the assembly and also is used to secure it in place. To increase the robustness of the repair multiple 3d tissue engineered constructs of EMT-primed satellite cells can be applied to the ventral hernia. The repair site is then covered with an appropriate surgical membrane and wound dressing to protect the wound and implanted tissue engineered device. Animals are then sampled at time points between initial wounding and 16 weeks.

In the rat model, inflammatory response, scarring and skeletal muscle regeneration can be assessed using histochemistry and immunohistochemistry (e.g., Pax7, MyoD, MF20 expression) of the repaired abdominal tissues using standard approaches. Functional assessment of live tissue from the repair can be done by taking regenerated muscle from the repair placing in a muscle bath, oxygenated (95% O2&5% C02) Krebs solution maintained at 37° C. at pH 7.4, and undertaking physiological tests of muscle function: isometric contraction, length/tension relationship determination, and breaking stress and strain. In human subjects, closure of the hernia, assessments of scarring and restoration of abdominal muscle function as assessed by a qualified clinician would be. Small biopsies of the repair can also be taken for direct assessment of muscle regeneration by histology by a qualified histotechnologist under the supervision of a clinician. However, it would be advisable to keep such invasive diagnoses to a minimum.

Methods

Provided herein are methods of promoting wound healing, organ or tissue replacement and tissue regeneration following injury, disease, surgery or congenital malformation in a subject, comprising administering to the subject one or more of the herein provided compositions (e.g., tissue engineered units with polypeptides, nucleic acids, or vectors or combinations of said units in three and two dimensional arrays).

The provided method can reduce scar tissue formation in a subject following tissue injury. By "scar tissue" is meant the fibrous (fibrotic) connective tissue that forms at the site of injury or disease in any tissue of the body, caused by the overproduction of disorganized collagen and other connective tissue proteins, which acts to patch the break in the tissue. Scar tissue may replace injured skin and underlying muscle, damaged heart muscle, or diseased areas of internal organs such as the liver. Dense and thick, it is usually paler than the surrounding tissue because it is poorly supplied with blood, and although it structurally replaces destroyed tissue, it cannot perform the functions of the missing tissue. It is composed of collagenous fibers, which will often restrict normal elasticity in the tissue involved. Scar tissue may therefore limit the range of muscle movement or prevent proper circulation of fluids when affecting the lymphatic or circulatory system. Glial scar tissue following injury to the brain or spinal chord is one of the main obstacles to restoration of neural function following damage to the central nervous system. A reduction in scar tissue can be assessed by the population of cell types within the injured site. For example, a reduction in glial scar tissue can be estimated by an increased ratio of neuronal to astrocytic cells. A reduction in scar tissue formation can be measured by a simple measurement of scar width or area of scar tissue (Wilgus et al., 2003). In addition histological assessments can be made about the restoration of structural complexity within healed tissue in comparison to normal tissue. The reduction in scar tissue can be partial or complete, meaning 10, 20, 30, 40, 50, 60, 70, 80, 90, 100% reduction, or any amount of reduction in between as compared to native or control levels.

In addition to reducing fibrotic tissue formation in a subject in following tissue injury, the provided compositions and methods can also be used to treat disorders associated with pathological increases in fibrotic tissue formation in a subject, such as for example, psoriasis, cutaneous and systemic mastocytosis, asthma, eczema, sinusitis, atherosclerosis, rheumatoid arthritis, inflammatory bowel disease, multiple sclerosis, pulmonary fibrosis and cystic fibrosis. A reduction in fibrotic tissue formation in a subject can be measured by clinical judgment of a doctor assessing whether a regain in normal structure and function of a given tissue and/or organ in a subject has resulted following a treatment. As an example, for psoriasis a doctor would assess the subject's skin to determine whether there has been a reduction in patches of raised red skin covered by flaky white buildup. Certain kinds of psoriasis, are characterized by a pimple-ish (pustular psoriasis) or burned (erythrodermic) appearance. In such cases, the doctor would determine whether treatment has resulted in the reduction of these symptoms. The reduction in fibrotic tissue can be partial or complete, meaning 10, 20, 30, 40, 50, 60, 70, 80, 90, 100% reduction, or any amount of reduction in between as compared to native or control levels. In the case of an tissue or organ in which a subject where a doctor judges that a biopsy is clinically available and/or necessary or in an animal model of the human disease, tissue fragments of biopsies would be prepared and tissue histological structure would be assessed by a clinical pathologist and/or trained histopathologist to determine if reduction in fibrosis and restoration of normal tissue structure and function has occurred. The area of fibrosis to normal tissue can also be quantitatively assessed on such histological preparations.

The provided method can improve tissue regeneration following tissue injury in a subject. By "regeneration" is meant the renewal, re-growth, or restoration of a body or a bodily part, tissue, or substance after injury or as a normal bodily process. In contrast to scarring, tissue regeneration involves the restoration of the tissue to its original structural, functional, and physiological condition. This is also referred to herein as tissue "complexity". The restoration can be partial or complete, meaning 10, 20, 30, 40, 50, 60, 70, 80, 90, 100% restoration, or any amount of restoration in between as compared to native or control levels. As an example, in the case of a skin injury, tissue regeneration can involve the restoration of hair follicles, glandular structures, blood vessels, muscle, or fat. In the case of a brain injury, tissue regeneration can involve maintenance or restoration of neurons. As an example in the case of skin an improvement in tissue regeneration can be assessed by measurements of the volume of fibrous scar tissue to normal regenerated skin as a ratio. As another example, counts can be made of discrete regenerating structures such as regenerating skin glands normalized to the volume of the wound area. As another example, counts of the density of cardiomyocytes can be made in the area of heart normally comprised of scar tissue following the healing of a myocardial infarction. Echocardiography can be used to measure the amount of recovery of cardiac function resulting from the regeneration of muscle cell in this scar tissue.

In one aspect, tissue regeneration involves the recruitment and differentiation of stem cells and/or progenitors cells to replace the damaged cells. These stem cells can be generated from the exogenous stem cells comprising the tissue engineered composition or be endogenous prompted by the composition to join, fuse or otherwise combine in the regenerative repair process. As used herein, a "stem cell" is an undifferentiated cell found among differentiated cells in a tissue or organ, or introduced as part of the tissue engineered composition as described elsewhere herein. The primary roles of stem cells in a living organism are to maintain and repair the tissue in which they are found. By stem cell differentiation is meant the process whereby an unspecialized cell (e.g., stem cell) acquires the features of a specialized cell such as a skin, neural, heart, liver, or muscle cell. As an example, in the case of a skin injury, tissue regeneration can involve the differentiation of stem cells present in the epithelium into hair follicles (Alonso and Fuchs, 2003). In the case of a brain injury, tissue regeneration can involve the differentiation of stem cells into neurons. In the case of a cardiac injury, tissue regeneration can involve the differentiation of stem cells into cardiomyocytes of various types (e.g., myocytes, conduction cells and nodal cells). The provided method can enhance stem cell differentiation following tissue injury in a subject. Enhanced stem cell differentiation can be measured by providing a clinically acceptable genetic or other means of marking endogenous or engrafted stem cells and determining the frequency of differentiation and incorporation of marked stem cells into normal tissue structures. The frequency of stem cell contribution to the repair can be partial or complete, meaning 1, 5, 10, 20, 30, 40, 50, 60, 70, 80, 90, 100% contribution, or any amount of contribution in between as compared to native or control levels. As another example, certain structures such as hair follicles are known to be regenerated from endogenous stem cells following tissue injury. As such, counts of marked stem cell derived hair follicles normalized to tissue injury area would serve as a quantitative assessment of enhanced stem cell differentiation. In a further example, marked resident stem cells in skeletal or cardiac muscle will be prompted to the contribute to the repair process. In another example, counts of the density of stem cell derived cardiomyocytes can be made in the area of heart normally comprised of scar tissue following the healing of a myocardial infarction.

The provided composition can reduce inflammation in a subject. By "inflammation", "inflammatory response" or "immune response" is meant the reaction of living tissues to injury, infection or irritation characterized by redness, warmth, swelling, pain, and loss of function, produced as the result of increased blood flow and an influx of immune cells and secretions. Inflammation is the body's reaction to invading infectious microorganisms and results in an increase in blood flow to the affected area, the release of chemicals that draw white blood cells, an increased flow of plasma, and the arrival of monocytes (or astrocytes in the case of the brain) to clean up the debris. Anything that stimulates the inflammatory response is said to be inflammatory. Thus, in addition to reducing inflammation in a subject in response to tissue injury, the provided compositions and methods can also be used to treat disorders associated with pathological increases in levels of inflammatory cells, including, for example, asthma, eczema, sinusitis, atherosclerosis, rheumatoid arthritis, inflammatory bowel disease, cutaneous and systemic mastocytosis, psoriasis, and multiple sclerosis. A reduction in inflammation can be measured by a reduction in the density of inflammatory cell types such as, for example, monocytes or astrocytes. A reduction in inflammation can be measured by a reduction in the density of inflammatory cell types such as, for example, neutrophils, macrophages, microglia, mast cells, basophils, and monocytes. A measurement can be measured by reductions in allied cells such myofibroblasts and the like. A reduction in inflammation can be calculated by an in vivo measurement of neutrophil activity (Jones et al., 1994). In addition factors like frequency of mast cell degranulation or measurement of histamine levels or levels of reactive oxygen species can be used as measurements of reduction in inflammation. The level of inflammation can also be indirectly measured by checking for transcription levels of certain genes by qRT-PCR for e.g. genes like, Interferon-alpha, -beta and -gamma, Tumor Necrosis Factor-alpha, Interleukine 1beta, -2, -4, -5, -6, -8, -12, -18, -23, -27, CD4, CD28, CD80, CD86, MHCII, and iNOS. Measurement of pro-inflammatory cytokine levels in the tissues and or bodily fluids of the subject including plasma can measure a reduction in inflammation. It is noteworthy that a mechanism of action may be by inhibition of inflammatory cell migration and/or inhibition of pro-inflammatory chemicals (histamine, reactive oxygen species) and pro-inflammatory cytokines such as Interleukin (IL)-1, IL-6, IL-8 and tumor necrosis factor (TNF). The reduction in inflammation can be partial or complete, meaning 10, 20, 30, 40, 50, 60, 70, 80, 90, 100% reduction, or any amount of reduction in between as compared to native or control levels.

As used herein, tissue injury can result from, for example, a cut, scrape, compression wound, stretch injury, laceration wound, crush wound, bite wound, graze, bullet wound, explosion injury, body piercing, stab wound, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, sex organ injury, joint injury, excretory organ injury, foot injury, finger injury, toe injury, bone injury, eye injury, corneal injury, muscle injury, adipose tissue injury, lung injury, airway injury, hernia, anus injury, piles, ear injury, skin injury, abdominal injury, retinal injury, eye injury, corneal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self mutilation, shock, traumatic soft tissue injury, spinal cord injury, spinal injury, sprain, strain, tendon injury, ligament injury, cartilage injury, thoracic injury, tooth injury, trauma, nervous system injury, burn wound, wind burn, sun burn, chemical burn, aging, aneurism, stroke, digestive tract injury, infarct, or ischemic injury.

It is understood that the disclosed compositions, devices and methods are not limited to the particular methodology, protocols, and reagents described as these can vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. Thus, for example, reference to "a peptide" includes a plurality of such polypeptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "~" and "about" one particular value, and/or to "~" and "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

"Pharmaceutically acceptable" is meant a material that is not biologically or otherwise undesirable, i.e., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

"Promote," "promotion," and "promoting" refer to an increase in an activity, response, condition, disease, or other biological parameter. This can include but is not limited to the initiation of the activity, response, condition, or disease. This can also include, for example, a 10% increase in the activity, response, condition, or disease as compared to the native or control level. Thus, the increase can be a 10, 20, 30, 40, 50, 60, 70, 80, 90, 100%, or any amount of increase in between as compared to native or control levels.

As used herein, "inhibit," "inhibiting," "inhibition" and "loss of function" mean to decrease an activity, response, condition, disease, or other biological parameter. This can include, but is not limited to, the complete loss of activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, agonizing, activating or gain of function mean to increase an activity, response, condition, disease, or other biological parameter. This can also include, for example, a 10% increase in the activity, response, condition, or disease as compared to the native or control level. Thus, the reduction can be a 10, 20, 30, 40, 50, 60, 70, 80, 90, 100%, 200%, 400% or any amount of increase in between as compared to native or control levels.

By "treat" or "treatment" is meant a method of reducing the effects of a disease or condition. Treatment can also refer to a method of reducing the underlying cause of the disease or condition itself rather than just the symptoms. The treatment can be any reduction from native levels and can be but is not limited to the complete ablation of the disease, condition, or the symptoms of the disease or condition. For example, a disclosed method for promoting wound healing is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels.

As used herein, "subject" includes, but is not limited to, animals, plants, bacteria, viruses, parasites and any other organism or entity that has nucleic acid. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

What is claimed:

1. A kit comprising: primed living bone-marrow stromal cells joined to and at least partially within a three-dimensional flexible hydrogel structure, the hydrogel structure comprising collagen and having a toroid shape; and an isolated polypeptide comprising the carboxy-terminal amino acid sequence of an alpha Connexin protein, or a conservative variant thereof, wherein the polypeptide does not comprise the full length alpha Connexin protein and the carboxy-terminal amino acid sequence is capable of inhibiting gap junction formation.

2. A method of forming a toroid, hydrogel structure comprising placing primed living bone marrow stromal cells on a three-dimensional, flexible hydrogel structure, the hydrogel structure comprising collagen, and permitting epithelialization of the cells in which the cells attach to the surface of the hydrogel structure, undergo epithelial mesenchymal transition and penetrate the surface of the hydrogel structure to form a toroid shape.

* * * * *